United States Patent
Imamura et al.

(10) Patent No.: US 7,282,481 B2
(45) Date of Patent: *Oct. 16, 2007

(54) HEPARIN-BINDING PROTEINS MODIFIED WITH SUGAR CHAINS, METHOD OF PRODUCING THE SAME AND PHARMACEUTICAL COMPOSITIONS CONTAINING SAME

(75) Inventors: Toru Imamura, Tokyo (JP); Masahiro Asada, Ibaraki (JP); Syuichi Oka, Ibaraki (JP); Masashi Suzuki, Ibaraki (JP); Atsuko Yoneda, Ibaraki (JP); Keiko Ota, Ibaraki (JP); Yuko Oda, Ibaraki (JP); Kazuko Miyakawa, Ibaraki (JP); Noriko Orikasa, Ibaraki (JP); Chie Asada, Ibaraki (JP); Tetsuhito Kojima, Aichi (JP)

(73) Assignee: Director-General of Agency of Industrial Science and Technology, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/285,798

(22) Filed: Nov. 23, 2005

(65) Prior Publication Data
US 2006/0079451 A1    Apr. 13, 2006

Related U.S. Application Data

(62) Division of application No. 09/121,017, filed on Jul. 22, 1998, now Pat. No. 7,005,415.

(30) Foreign Application Priority Data
Nov. 10, 1997  (JP) .............................. 1997-307721

(51) Int. Cl.
*A61K 38/18*  (2006.01)
*C07K 14/475*  (2006.01)

(52) U.S. Cl. .......................... 514/8; 530/395; 530/396; 530/399; 530/402; 530/404; 530/408; 530/411

(58) Field of Classification Search .................... 514/8; 530/395, 396, 399, 402, 404, 408, 411
See application file for complete search history.

(56) References Cited

U.S. PATENT DOCUMENTS

| | | | |
|---|---|---|---|
| 4,280,953 A | 7/1981 | Guillemin et al. | |
| 4,478,746 A | 10/1984 | Kim et al. | |
| 5,360,896 A | 11/1994 | Senoo et al. | |
| 5,486,599 A | 1/1996 | Saunders et al. | |
| 7,005,415 B1 * | 2/2006 | Imamura et al. ............... | 514/8 |

FOREIGN PATENT DOCUMENTS

| | | |
|---|---|---|
| WO | WO8801647 | 3/1988 |
| WO | WO9116335 | 10/1991 |

OTHER PUBLICATIONS

Jaye et al., Science vol. 233, pp. 541-544, Aug. 1986.
Imamura, et al., Science, vol. 249, pp. 1567-1570, Sep. 1990.

* cited by examiner

*Primary Examiner*—David A. Saunders
(74) *Attorney, Agent, or Firm*—Davidson, Davidson & Kappel, LLC

(57) ABSTRACT

A heparin-binding protein functionalized by covalently bonding thereto a sugar chain, a method for producing the protein and a pharmaceutical composition containing the protein as an active ingredient, as well as a method of functionalizing a natural protein having no sugar chain by covalently bonding thereto a sugar chain.

10 Claims, 9 Drawing Sheets

1) High Mannose Type

2) Complex Type

3) Hybrid Type

A) SDS-Denatured Electrophoregram of S/FGF-1a-II Protein

B) SDS-Denatured Electrophoregrams of N-FGF-1a-IV and O-FGF-1a Proteins

Lane a: FGF-1a produced in *E. coli*
Lane b: N-FGF-6/1a-II treated with peptide N-glycosidase F to remove N-linked sugar chains
Lane c: N-FGF-6/1a-II
Lane d: O-FGF-6/1a

SEQUENCE LISTING

```
<160> NUMBER OF SEQ ID NOS: 31

<210> SEQ ID NO 1
<211> LENGTH: 221
<212> TYPE: PRT
<213> ORGANISM: Artificial Sequence
<220> FEATURE:
<223> OTHER INFORMATION: Description of Artificial Sequence: fusion of
      sequence for a part of human rydocan and a part of human
      fibroblast growth factor 1

<400> SEQUENCE: 1

Met Ala Pro Ala Arg Leu Phe Ala Leu Leu Leu Phe Phe Val Gly Gly
 1               5                  10                  15

Val Ala Glu Ser Ile Arg Glu Thr Glu Val Ile Asp Pro Gln Asp Leu
            20                  25                  30
```

```
Leu Glu Gly Arg Tyr Phe Ser Gly Ala Leu Pro Asp Asp Glu Asp Val
             35                  40                  45

Val Gly Pro Gly Gln Glu Ser Asp Asp Phe Glu Leu Ser Gly Ser Gly
 50                  55                  60

Asp Leu Asp Asp Leu Glu Asp Ser Met Ile Gly Pro Glu Val Val His
 65                  70                  75                  80

Pro Leu Val Pro Leu Asp Ala Asn Tyr Lys Lys Pro Lys Leu Leu Tyr
                 85                  90                  95

Cys Ser Asn Gly Gly His Phe Leu Arg Ile Leu Pro Asp Gly Thr Val
                100                 105                 110

Asp Gly Thr Arg Asp Arg Ser Asp Gln His Ile Gln Leu Gln Leu Ser
            115                 120                 125

Ala Glu Ser Val Gly Glu Val Tyr Ile Lys Ser Thr Glu Thr Gly Gln
    130                 135                 140

Tyr Leu Ala Met Asp Thr Asp Gly Leu Leu Tyr Gly Ser Gln Thr Pro
145                 150                 155                 160

Asn Glu Glu Cys Leu Phe Leu Glu Arg Leu Glu Glu Asn His Tyr Asn
                165                 170                 175

Thr Tyr Ile Ser Lys Lys His Ala Glu Lys Asn Trp Phe Val Gly Leu
                180                 185                 190

Lys Lys Asn Gly Ser Cys Lys Arg Gly Pro Arg Thr His Tyr Gly Gln
            195                 200                 205

Lys Ala Ile Leu Phe Leu Pro Leu Pro Val Ser Ser Asp
            210                 215                 220

<210> SEQ ID NO 2
<211> LENGTH: 663
<212> TYPE: DNA
<213> ORGANISM: Artificial Sequence
<220> FEATURE:
<223> OTHER INFORMATION: Description of Artificial Sequence: fusion of
      sequence for a part of human rydocan and a part of human
      fibroblast growth factor 1
<220> FEATURE:
<221> NAME/KEY: CDS
<222> LOCATION: (1)..(663)

<400> SEQUENCE: 2 atg gcc ccc gcc cgt ctg ttc gcg ctg ctg ctg ttc ttc gta ggc gga      48
Met Ala Pro Ala Arg Leu Phe Ala Leu Leu Leu Phe Phe Val Gly Gly
 1               5                  10                  15 gtc gcc gag tcg atc cga gag act gag gtc atc gac ccc cag gac ctc      96
Val Ala Glu Ser Ile Arg Glu Thr Glu Val Ile Asp Pro Gln Asp Leu
             20                  25                  30 cta gaa ggc cga tac ttc tcc gga gcc cta cca gac gat gag gat gta     144
Leu Glu Gly Arg Tyr Phe Ser Gly Ala Leu Pro Asp Asp Glu Asp Val
         35                  40                  45 gtg ggg ccc ggg cag gaa tct gat gac ttt gag ctg tct ggc tct gga     192
Val Gly Pro Gly Gln Glu Ser Asp Asp Phe Glu Leu Ser Gly Ser Gly
 50                  55                  60 gat ctg gat gac ttg gaa gac tcc atg atc ggc cct gaa gtt gtc cat     240
Asp Leu Asp Asp Leu Glu Asp Ser Met Ile Gly Pro Glu Val Val His
 65                  70                  75                  80 ccc ttg gtg cct cta gat gct aat tac aag aag ccc aaa ctc ctc tac     288
Pro Leu Val Pro Leu Asp Ala Asn Tyr Lys Lys Pro Lys Leu Leu Tyr
                 85                  90                  95 tgt agc aac ggg ggc cac ttc ctg agg atc ctt ccg gat ggc aca gtg     336
Cys Ser Asn Gly Gly His Phe Leu Arg Ile Leu Pro Asp Gly Thr Val
                100                 105                 110
```

```
gat ggg aca agg gac agg agc gac cag cac att cag ctg cag ctc agt      384
Asp Gly Thr Arg Asp Arg Ser Asp Gln His Ile Gln Leu Gln Leu Ser
            115                 120                 125 gcg gaa agc gtg ggg gag gtg tat ata aag agt acc gag act ggc cag      432
Ala Glu Ser Val Gly Glu Val Tyr Ile Lys Ser Thr Glu Thr Gly Gln
130                 135                 140 tac ttg gcc atg gac acc gac ggg ctt tta tac ggc tca cag aca cca      480
Tyr Leu Ala Met Asp Thr Asp Gly Leu Leu Tyr Gly Ser Gln Thr Pro
145                 150                 155                 160 aat gag gaa tgt ttg ttc ctg gaa agg ctg gag gag aac cat tac aac      528
Asn Glu Glu Cys Leu Phe Leu Glu Arg Leu Glu Glu Asn His Tyr Asn
            165                 170                 175 acc tat ata tcc aag aag cat gca gag aag aat tgg ttt gtt ggc ctc      576
Thr Tyr Ile Ser Lys Lys His Ala Glu Lys Asn Trp Phe Val Gly Leu
            180                 185                 190 aag aag aat ggg agc tgc aaa cgc ggt cct cgg act cac tat ggc cag      624
Lys Lys Asn Gly Ser Cys Lys Arg Gly Pro Arg Thr His Tyr Gly Gln
            195                 200                 205 aaa gca atc ttg ttt ctc ccc ctg cca gtc tct tct gat                  663
Lys Ala Ile Leu Phe Leu Pro Leu Pro Val Ser Ser Asp
210                 215                 220

<210> SEQ ID NO 3
<211> LENGTH: 175
<212> TYPE: PRT
<213> ORGANISM: Artificial Sequence
<220> FEATURE:
<223> OTHER INFORMATION: Description of Artificial Sequence: fusion of
      sequence for a part of mouse fibroblast growth factor 6 and
      a part of human fibroblast growth factor 1

<400> SEQUENCE: 3

Met Ser Arg Gly Ala Gly Arg Val Gln Gly Thr Leu Gln Ala Leu Val
1               5                   10                  15

Phe Leu Gly Val Leu Val Gly Met Val Val Pro Ser Pro Ala Gly Ala
            20                  25                  30

Arg Ala Asn Gly Thr Leu Leu Asp Ala Asn Tyr Lys Lys Pro Lys Leu
        35                  40                  45

Leu Tyr Cys Ser Asn Gly Gly His Phe Leu Arg Ile Leu Pro Asp Gly
    50                  55                  60

Thr Val Asp Gly Thr Arg Asp Arg Ser Asp Gln His Ile Gln Leu Gln
65                  70                  75                  80

Leu Ser Ala Glu Ser Val Gly Glu Val Tyr Ile Lys Ser Thr Glu Thr
                85                  90                  95

Gly Gln Tyr Leu Ala Met Asp Thr Asp Gly Leu Leu Tyr Gly Ser Gln
            100                 105                 110

Thr Pro Asn Glu Glu Cys Leu Phe Leu Glu Arg Leu Glu Glu Asn His
        115                 120                 125

Tyr Asn Thr Tyr Ile Ser Lys Lys His Ala Glu Lys Asn Trp Phe Val
    130                 135                 140

Gly Leu Lys Lys Asn Gly Ser Cys Lys Arg Gly Pro Arg Thr His Tyr
145                 150                 155                 160

Gly Gln Lys Ala Ile Leu Phe Leu Pro Leu Pro Val Ser Ser Asp
                165                 170                 175

<210> SEQ ID NO 4
<211> LENGTH: 525
<212> TYPE: DNA
<213> ORGANISM: Artificial Sequence
```

<220> FEATURE:
<223> OTHER INFORMATION: Description of Artificial Sequence: fusion of
sequence for a part of mouse fibroblast growth factor 6 and
a part of human fibroblast growth factor 1
<220> FEATURE:
<221> NAME/KEY: CDS
<222> LOCATION: (1)..(525)

<400> SEQUENCE: 4

```
atg tcc cgg gga gca gga cgt gtt cag ggc acg ctg cag gct ctc gtc      48
Met Ser Arg Gly Ala Gly Arg Val Gln Gly Thr Leu Gln Ala Leu Val
 1               5                  10                  15 ttc tta ggc gtc cta gtg ggc atg gtg gtg ccc tca cct gcc ggc gcc      96
Phe Leu Gly Val Leu Val Gly Met Val Val Pro Ser Pro Ala Gly Ala
             20                  25                  30 cgc gcc aac ggc acg cta ctg gac gct aat tac aag aag ccc aaa ctc     144
Arg Ala Asn Gly Thr Leu Leu Asp Ala Asn Tyr Lys Lys Pro Lys Leu
         35                  40                  45 ctc tac tgt agc aac ggg ggc cac ttc ctg agg atc ctt ccg gat ggc     192
Leu Tyr Cys Ser Asn Gly Gly His Phe Leu Arg Ile Leu Pro Asp Gly
     50                  55                  60 aca gtg gat ggg aca agg gac agg agc gac cag cac att cag ctg cag     240
Thr Val Asp Gly Thr Arg Asp Arg Ser Asp Gln His Ile Gln Leu Gln
 65                  70                  75                  80 ctc agt gcg gaa agc gtg ggg gag gtg tat ata aag agt acc gag act     288
Leu Ser Ala Glu Ser Val Gly Glu Val Tyr Ile Lys Ser Thr Glu Thr
                 85                  90                  95 ggc cag tac ttg gcc atg gac acc gac ggg ctt tta tac ggc tca cag     336
Gly Gln Tyr Leu Ala Met Asp Thr Asp Gly Leu Leu Tyr Gly Ser Gln
            100                 105                 110 aca cca aat gag gaa tgt ttg ttc ctg gaa agg ctg gag gag aac cat     384
Thr Pro Asn Glu Glu Cys Leu Phe Leu Glu Arg Leu Glu Glu Asn His
        115                 120                 125 tac aac acc tat ata tcc aag aag cat gca gag aag aat tgg ttt gtt     432
Tyr Asn Thr Tyr Ile Ser Lys Lys His Ala Glu Lys Asn Trp Phe Val
    130                 135                 140 ggc ctc aag aag aat ggg agc tgc aaa cgc ggt cct cgg act cac tat     480
Gly Leu Lys Lys Asn Gly Ser Cys Lys Arg Gly Pro Arg Thr His Tyr
145                 150                 155                 160 ggc cag aaa gca atc ttg ttt ctc ccc ctg cca gtc tct tct gat         525
Gly Gln Lys Ala Ile Leu Phe Leu Pro Leu Pro Val Ser Ser Asp
                165                 170                 175
```

<210> SEQ ID NO 5
<211> LENGTH: 181
<212> TYPE: PRT
<213> ORGANISM: Artificial Sequence
<220> FEATURE:
<223> OTHER INFORMATION: Description of Artificial Sequence: fusion of
sequence for a part of mouse fibroblast growth factor 6,
a part of human fibroblast growth factor 1 and an artificial
sequence

<400> SEQUENCE: 5

```
Met Ser Arg Gly Ala Gly Arg Val Gln Gly Thr Leu Gln Ala Leu Val
 1               5                  10                  15

Phe Leu Gly Val Leu Val Gly Met Val Val Pro Ser Pro Ala Gly Ala
             20                  25                  30

Arg Ala Gln Gly Thr Leu Leu Asp Ala Asn Tyr Lys Lys Pro Lys Leu
         35                  40                  45

Leu Tyr Cys Ser Asn Gly Gly His Phe Leu Arg Ile Leu Pro Asp Gly
     50                  55                  60
```

```
Thr Val Asp Gly Thr Arg Asp Arg Ser Asp Gln His Ile Gln Leu Gln
 65                  70                  75                  80

Leu Ser Ala Glu Ser Val Gly Glu Val Tyr Ile Lys Ser Thr Glu Thr
                 85                  90                  95

Gly Gln Tyr Leu Ala Met Asp Thr Asp Gly Leu Leu Tyr Gly Ser Gln
            100                 105                 110

Thr Pro Asn Glu Glu Cys Leu Phe Leu Glu Arg Leu Glu Glu Ala Ala
            115                 120                 125

Thr Pro Ala Pro Asn His Tyr Asn Thr Tyr Ile Ser Lys Lys His Ala
        130                 135                 140

Glu Lys Asn Trp Phe Val Gly Leu Lys Lys Asn Gly Ser Cys Lys Arg
145                 150                 155                 160

Gly Pro Arg Thr His Tyr Gly Gln Lys Ala Ile Leu Phe Leu Pro Leu
                165                 170                 175

Pro Val Ser Ser Asp
            180

<210> SEQ ID NO 6
<211> LENGTH: 543
<212> TYPE: DNA
<213> ORGANISM: Artificial Sequence
<220> FEATURE:
<223> OTHER INFORMATION: Description of Artificial Sequence: fusion of
      sequence for a part of mouse fibroblast growth factor 6,
      a part of human fibroblast growth factor 1 and an artificial
      sequence
<220> FEATURE:
<221> NAME/KEY: CDS
<222> LOCATION: (1)..(543)

<400> SEQUENCE: 6 atg tcc cgg gga gca gga cgt gtt cag ggc acg ctg cag gct ctc gtc      48
Met Ser Arg Gly Ala Gly Arg Val Gln Gly Thr Leu Gln Ala Leu Val
 1               5                  10                  15 ttc tta ggc gtc cta gtg ggc atg gtg gtg ccc tca cct gcc ggc gcc      96
Phe Leu Gly Val Leu Val Gly Met Val Val Pro Ser Pro Ala Gly Ala
             20                  25                  30 cgc gcc caa ggc acg cta ctg gac gct aat tac aag aag ccc aaa ctc     144
Arg Ala Gln Gly Thr Leu Leu Asp Ala Asn Tyr Lys Lys Pro Lys Leu
         35                  40                  45 ctc tac tgt agc aac ggg ggc cac ttc ctg agg atc ctt ccg gat ggc     192
Leu Tyr Cys Ser Asn Gly Gly His Phe Leu Arg Ile Leu Pro Asp Gly
     50                  55                  60 aca gtg gat ggg aca agg gac agg agc gac cag cac att cag ctg cag     240
Thr Val Asp Gly Thr Arg Asp Arg Ser Asp Gln His Ile Gln Leu Gln
 65                  70                  75                  80 ctc agt gcg gaa agc gtg ggg gag gtg tat ata aag agt acc gag act     288
Leu Ser Ala Glu Ser Val Gly Glu Val Tyr Ile Lys Ser Thr Glu Thr
                 85                  90                  95 ggc cag tac ttg gcc atg gac acc gac ggg ctt tta tac ggc tca cag     336
Gly Gln Tyr Leu Ala Met Asp Thr Asp Gly Leu Leu Tyr Gly Ser Gln
            100                 105                 110 aca cca aat gag gaa tgt ttg ttc ctg gaa agg ctg gag gag gct gct     384
Thr Pro Asn Glu Glu Cys Leu Phe Leu Glu Arg Leu Glu Glu Ala Ala
            115                 120                 125 act cca gct cca aac cat tac aac acc tat ata tcc aag aag cat gca     432
Thr Pro Ala Pro Asn His Tyr Asn Thr Tyr Ile Ser Lys Lys His Ala
        130                 135                 140 gag aag aat tgg ttt gtt ggc ctc aag aag aat ggg agc tgc aaa cgc     480
Glu Lys Asn Trp Phe Val Gly Leu Lys Lys Asn Gly Ser Cys Lys Arg
145                 150                 155                 160
```

```
ggt cct cgg act cac tat ggc cag aaa gca atc ttg ttt ctc ccc ctg      528
Gly Pro Arg Thr His Tyr Gly Gln Lys Ala Ile Leu Phe Leu Pro Leu
            165                 170                 175 cca gtc tct tct gat                                                   543
Pro Val Ser Ser Asp
            180
```

```
<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:primer for
      PCR

<400> SEQUENCE: 7
ttgtcgaccc accatggccc cgcccgtct                                        30

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:primer for
      PCR

<400> SEQUENCE: 8
ttgatatcta gaggcaccaa gggatg                                           26

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence:primer for
      PCR

<400> SEQUENCE: 9
gcgtcgacag cgctaattac aagaagccca aactc                                 35

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence:primer for
      PCR

<400> SEQUENCE: 10
ccgaattcga attctttaat cagaagagac tgg                                   33

<210> SEQ ID NO 11
<211> LENGTH: 64
<212> TYPE: DNA
<213> ORGANISM: Artificial Sequence
<220> FEATURE:
<223> OTHER INFORMATION: Description of Artificial Sequence:primer for
      PCR

<400> SEQUENCE: 11
gcgtcgaccc accatgtccc ggggagcagg acgtgttcag ggcacgctgc aggctctcgt      60
cttc                                                                   64

<210> SEQ ID NO 12
<211> LENGTH: 29
```

```
<212> TYPE: DNA
<213> ORGANISM: Artificial Sequence
<220> FEATURE:
<223> OTHER INFORMATION: Description of Artificial Sequence:primer for
      PCR

<400> SEQUENCE: 12
gcgatatcca gtagcgtgcc gttggcgcg                                    29

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:primer for
      PCR

<400> SEQUENCE: 13
gcgtcgaccc accatgtc                                                18

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:primer for
      PCR

<400> SEQUENCE: 14
gcgatatcca gtagcgtgcc ttgggcgcg                                    29

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence:primer for
      PCR

<400> SEQUENCE: 15
gctggaggag gctgctactc cagctccaaa ccattaca                          38

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:primer for
      PCR

<400> SEQUENCE: 16
gccgctctag aactagtgga t                                            21

<210> SEQ ID NO 17
<211> LENGTH: 200
<212> TYPE: PRT
<213> ORGANISM: Artificial Sequence
<220> FEATURE:
<223> OTHER INFORMATION: Description of Artificial Sequence: fusion of
      sequence for a part of human ryudocan and a part of human
      fibroblast growth factor 1

<400> SEQUENCE: 17

Met Ala Pro Ala Arg Leu Phe Ala Leu Leu Leu Phe Phe Val Gly Gly
 1               5                  10                  15

Val Ala Glu Ser Ile Arg Glu Thr Glu Val Ile Asp Pro Gln Asp Leu
            20                  25                  30
```

```
Leu Glu Gly Arg Tyr Phe Ser Gly Ala Leu Pro Asp Asp Glu Asp Val
         35                  40                  45

Val Gly Pro Gly Gln Glu Ser Asp Asp Phe Glu Leu Ser Gly Ser Gly
 50                  55                  60

Asp Ala Asn Tyr Lys Lys Pro Lys Leu Leu Tyr Cys Ser Asn Gly Gly
 65                  70                  75                  80

His Phe Leu Arg Ile Leu Pro Asp Gly Thr Val Asp Gly Thr Arg Asp
                 85                  90                  95

Arg Ser Asp Gln His Ile Gln Leu Gln Leu Ser Ala Glu Ser Val Gly
             100                 105                 110

Glu Val Tyr Ile Lys Ser Thr Glu Thr Gly Gln Tyr Leu Ala Met Asp
         115                 120                 125

Thr Asp Gly Leu Leu Tyr Gly Ser Gln Thr Pro Asn Glu Glu Cys Leu
 130                 135                 140

Phe Leu Glu Arg Leu Glu Glu Asn His Tyr Asn Thr Tyr Ile Ser Lys
145                 150                 155                 160

Lys His Ala Glu Lys Asn Trp Phe Val Gly Leu Lys Lys Asn Gly Ser
                 165                 170                 175

Cys Lys Arg Gly Pro Arg Thr His Tyr Gly Gln Lys Ala Ile Leu Phe
             180                 185                 190

Leu Pro Leu Pro Val Ser Ser Asp
         195                 200

<210> SEQ ID NO 18
<211> LENGTH: 600
<212> TYPE: DNA
<213> ORGANISM: Artificial Sequence
<220> FEATURE:
<223> OTHER INFORMATION: Description of Artificial Sequence: fusion of
      sequence for a part of human ryudocan and a part of human
      fibroblast growth factor 1
<220> FEATURE:
<221> NAME/KEY: CDS
<222> LOCATION: (1)..(600)

<400> SEQUENCE: 18 atg gcc ccc gcc cgt ctg ttc gcg ctg ctg ctg ttc ttc gta ggc gga      48
Met Ala Pro Ala Arg Leu Phe Ala Leu Leu Leu Phe Phe Val Gly Gly
 1               5                  10                  15 gtc gcc gag tcg atc cga gag act gag gtc atc gac ccc cag gac ctc      96
Val Ala Glu Ser Ile Arg Glu Thr Glu Val Ile Asp Pro Gln Asp Leu
             20                  25                  30 cta gaa ggc cga tac ttc tcc gga gcc cta cca gac gat gag gat gta     144
Leu Glu Gly Arg Tyr Phe Ser Gly Ala Leu Pro Asp Asp Glu Asp Val
         35                  40                  45 gtg ggg ccc ggg cag gaa tct gat gac ttt gag ctg tct ggc tct gga     192
Val Gly Pro Gly Gln Glu Ser Asp Asp Phe Glu Leu Ser Gly Ser Gly
 50                  55                  60 gat gct aat tac aag aag ccc aaa ctc ctc tac tgt agc aac ggg ggc     240
Asp Ala Asn Tyr Lys Lys Pro Lys Leu Leu Tyr Cys Ser Asn Gly Gly
 65                  70                  75                  80 cac ttc ctg agg atc ctt ccg gat ggc aca gtg gat ggg aca agg gac     288
His Phe Leu Arg Ile Leu Pro Asp Gly Thr Val Asp Gly Thr Arg Asp
                 85                  90                  95 agg agc gac cag cac att cag ctg cag ctc agt gcg gaa agc gtg ggg     336
Arg Ser Asp Gln His Ile Gln Leu Gln Leu Ser Ala Glu Ser Val Gly
             100                 105                 110 gag gtg tat ata aag agt acc gag act ggc cag tac ttg gcc atg gac     384
Glu Val Tyr Ile Lys Ser Thr Glu Thr Gly Gln Tyr Leu Ala Met Asp
         115                 120                 125
```

```
acc gac ggg ctt tta tac ggc tca cag aca cca aat gag gaa tgt ttg    432
Thr Asp Gly Leu Leu Tyr Gly Ser Gln Thr Pro Asn Glu Glu Cys Leu
    130                 135                 140 ttc ctg gaa agg ctg gag gag aac cat tac aac acc tat ata tcc aag    480
Phe Leu Glu Arg Leu Glu Glu Asn His Tyr Asn Thr Tyr Ile Ser Lys
145                 150                 155                 160 aag cat gca gag aag aat tgg ttt gtt ggc ctc aag aag aat ggg agc    528
Lys His Ala Glu Lys Asn Trp Phe Val Gly Leu Lys Lys Asn Gly Ser
                165                 170                 175 tgc aaa cgc ggt cct cgg act cac tat ggc cag aaa gca atc ttg ttt    576
Cys Lys Arg Gly Pro Arg Thr His Tyr Gly Gln Lys Ala Ile Leu Phe
            180                 185                 190 ctc ccc ctg cca gtc tct tct gat                                    600
Leu Pro Leu Pro Val Ser Ser Asp
            195                 200
```

<210> SEQ ID NO 19
<211> LENGTH: 200
<212> TYPE: PRT
<213> ORGANISM: Artificial Sequence
<220> FEATURE:
<223> OTHER INFORMATION: Description of Artificial Sequence: fusion of
      sequence for a part of human ryudocan mutant and a part of human
      fibroblast growth factor 1

<400> SEQUENCE: 19

```
Met Ala Pro Ala Arg Leu Phe Ala Leu Leu Leu Phe Phe Val Gly Gly
1               5                   10                  15

Val Ala Glu Ser Ile Arg Glu Thr Glu Val Ile Asp Pro Gln Asp Leu
            20                  25                  30

Leu Glu Gly Arg Tyr Phe Ser Gly Ala Leu Ser Asp Asp Glu Asp Val
        35                  40                  45

Val Gly Pro Gly Gln Glu Ser Asp Asp Phe Glu Leu Ser Gly Ser Gly
    50                  55                  60

Asp Ala Asn Tyr Lys Lys Pro Lys Leu Leu Tyr Cys Ser Asn Gly Gly
65                  70                  75                  80

His Phe Leu Arg Ile Leu Pro Asp Gly Thr Val Asp Gly Thr Arg Asp
                85                  90                  95

Arg Ser Asp Gln His Ile Gln Leu Gln Leu Ser Ala Glu Ser Val Gly
            100                 105                 110

Glu Val Tyr Ile Lys Ser Thr Glu Thr Gly Gln Tyr Leu Ala Met Asp
        115                 120                 125

Thr Asp Gly Leu Leu Tyr Gly Ser Gln Thr Pro Asn Glu Glu Cys Leu
    130                 135                 140

Phe Leu Glu Arg Leu Glu Glu Asn His Tyr Asn Thr Tyr Ile Ser Lys
145                 150                 155                 160

Lys His Ala Glu Lys Asn Trp Phe Val Gly Leu Lys Lys Asn Gly Ser
                165                 170                 175

Cys Lys Arg Gly Pro Arg Thr His Tyr Gly Gln Lys Ala Ile Leu Phe
            180                 185                 190

Leu Pro Leu Pro Val Ser Ser Asp
        195                 200
```

<210> SEQ ID NO 20
<211> LENGTH: 600
<212> TYPE: DNA
<213> ORGANISM: Artificial Sequence
<220> FEATURE:

<223> OTHER INFORMATION: Description of Artificial Sequence: fusion of
      sequence for a part of human ryudocan mutant and a part of human
      fibroblast growth factor 1
<220> FEATURE:
<221> NAME/KEY: CDS
<222> LOCATION: (1)..(600)

<400> SEQUENCE: 20

```
atg gcc ccc gcc cgt ctg ttc gcg ctg ctg ctg ttc ttc gta ggc gga      48
Met Ala Pro Ala Arg Leu Phe Ala Leu Leu Leu Phe Phe Val Gly Gly
 1               5                  10                  15 gtc gcc gag tcg atc cga gag act gag gtc atc gac ccc cag gac ctc      96
Val Ala Glu Ser Ile Arg Glu Thr Glu Val Ile Asp Pro Gln Asp Leu
                20                  25                  30 cta gaa ggc cga tac ttc tcc gga gcc cta tca gac gat gag gat gta     144
Leu Glu Gly Arg Tyr Phe Ser Gly Ala Leu Ser Asp Asp Glu Asp Val
            35                  40                  45 gtg ggg ccc ggg cag gaa tct gat gac ttt gag ctg tct ggc tct gga     192
Val Gly Pro Gly Gln Glu Ser Asp Asp Phe Glu Leu Ser Gly Ser Gly
    50                  55                  60 gat gct aat tac aag aag ccc aaa ctc ctc tac tgt agc aac ggg ggc     240
Asp Ala Asn Tyr Lys Lys Pro Lys Leu Leu Tyr Cys Ser Asn Gly Gly
65                  70                  75                  80 cac ttc ctg agg atc ctt ccg gat ggc aca gtg gat ggg aca agg gac     288
His Phe Leu Arg Ile Leu Pro Asp Gly Thr Val Asp Gly Thr Arg Asp
                85                  90                  95 agg agc gac cag cac att cag ctg cag ctc agt gcg gaa agc gtg ggg     336
Arg Ser Asp Gln His Ile Gln Leu Gln Leu Ser Ala Glu Ser Val Gly
               100                 105                 110 gag gtg tat ata aag agt acc gag act ggc cag tac ttg gcc atg gac     384
Glu Val Tyr Ile Lys Ser Thr Glu Thr Gly Gln Tyr Leu Ala Met Asp
           115                 120                 125 acc gac ggg ctt tta tac ggc tca cag aca cca aat gag gaa tgt ttg     432
Thr Asp Gly Leu Leu Tyr Gly Ser Gln Thr Pro Asn Glu Glu Cys Leu
   130                 135                 140 ttc ctg gaa agg ctg gag gag aac cat tac aac acc tat ata tcc aag     480
Phe Leu Glu Arg Leu Glu Glu Asn His Tyr Asn Thr Tyr Ile Ser Lys
145                 150                 155                 160 aag cat gca gag aag aat tgg ttt gtt ggc ctc aag aag aat ggg agc     528
Lys His Ala Glu Lys Asn Trp Phe Val Gly Leu Lys Lys Asn Gly Ser
                165                 170                 175 tgc aaa cgc ggt cct cgg act cac tat ggc cag aaa gca atc ttg ttt     576
Cys Lys Arg Gly Pro Arg Thr His Tyr Gly Gln Lys Ala Ile Leu Phe
            180                 185                 190 ctc ccc ctg cca gtc tct tct gat                                     600
Leu Pro Leu Pro Val Ser Ser Asp
        195                 200
```

<210> SEQ ID NO 21
<211> LENGTH: 254
<212> TYPE: PRT
<213> ORGANISM: Artificial Sequence
<220> FEATURE:
<223> OTHER INFORMATION: Description of Artificial Sequence: fusion of
      sequence for a part of human ryudocan and a part of human
      fibroblast growth factor 1

<400> SEQUENCE: 21

```
Met Ala Pro Ala Arg Leu Phe Ala Leu Leu Leu Phe Phe Val Gly Gly
 1               5                  10                  15

Val Ala Glu Ser Ile Arg Glu Thr Glu Val Ile Asp Pro Gln Asp Leu
                20                  25                  30
```

```
Leu Glu Gly Arg Tyr Phe Ser Gly Ala Leu Pro Asp Asp Glu Asp Val
             35                  40                  45

Val Gly Pro Gly Gln Glu Ser Asp Asp Phe Glu Leu Ser Gly Ser Gly
     50                  55                  60

Asp Leu Asp Asp Leu Glu Asp Ser Met Ile Gly Pro Glu Val Val His
 65                  70                  75                  80

Pro Leu Val Pro Leu Asp Asn His Ile Pro Glu Arg Ala Gly Ser Gly
                 85                  90                  95

Ser Gln Val Pro Thr Glu Pro Lys Lys Leu Glu Glu Asn Glu Val Ile
             100                 105                 110

Pro Lys Arg Ile Ser Pro Val Ala Asn Tyr Lys Lys Pro Lys Leu Leu
         115                 120                 125

Tyr Cys Ser Asn Gly Gly His Phe Leu Arg Ile Leu Pro Asp Gly Thr
     130                 135                 140

Val Asp Gly Thr Arg Asp Arg Ser Asp Gln His Ile Gln Leu Gln Leu
145                 150                 155                 160

Ser Ala Glu Ser Val Gly Glu Val Tyr Ile Lys Ser Thr Glu Thr Gly
                 165                 170                 175

Gln Tyr Leu Ala Met Asp Thr Asp Gly Leu Leu Tyr Gly Ser Gln Thr
             180                 185                 190

Pro Asn Glu Glu Cys Leu Phe Leu Glu Arg Leu Glu Glu Asn His Tyr
         195                 200                 205

Asn Thr Tyr Ile Ser Lys Lys His Ala Glu Lys Asn Trp Phe Val Gly
     210                 215                 220

Leu Lys Lys Asn Gly Ser Cys Lys Arg Gly Pro Arg Thr His Tyr Gly
225                 230                 235                 240

Gln Lys Ala Ile Leu Phe Leu Pro Leu Pro Val Ser Ser Asp
                 245                 250

<210> SEQ ID NO 22
<211> LENGTH: 762
<212> TYPE: DNA
<213> ORGANISM: Artificial Sequence
<220> FEATURE:
<223> OTHER INFORMATION: Description of Artificial Sequence: fusion of
      sequence for a part of human ryudocan and a part of human
      fibroblast growth factor 1
<220> FEATURE:
<221> NAME/KEY: CDS
<222> LOCATION: (1)..(762)

<400> SEQUENCE: 22 atg gcc ccc gcc cgt ctg ttc gcg ctg ctg ctg ttc ttc gta ggc gga      48
Met Ala Pro Ala Arg Leu Phe Ala Leu Leu Leu Phe Phe Val Gly Gly
 1               5                  10                  15 gtc gcc gag tcg atc cga gag act gag gtc atc gac ccc cag gac ctc      96
Val Ala Glu Ser Ile Arg Glu Thr Glu Val Ile Asp Pro Gln Asp Leu
             20                  25                  30 cta gaa ggc cga tac ttc tcc gga gcc cta cca gac gat gag gat gta     144
Leu Glu Gly Arg Tyr Phe Ser Gly Ala Leu Pro Asp Asp Glu Asp Val
         35                  40                  45 gtg ggg ccc ggg cag gaa tct gat gac ttt gag ctg tct ggc tct gga     192
Val Gly Pro Gly Gln Glu Ser Asp Asp Phe Glu Leu Ser Gly Ser Gly
     50                  55                  60 gat ctg gat gac ttg gaa gac tcc atg atc ggc cct gaa gtt gtc cat     240
Asp Leu Asp Asp Leu Glu Asp Ser Met Ile Gly Pro Glu Val Val His
 65                  70                  75                  80 ccc ttg gtg cct cta gat aac cat atc cct gag agg gca ggg tct ggg     288
Pro Leu Val Pro Leu Asp Asn His Ile Pro Glu Arg Ala Gly Ser Gly
                 85                  90                  95
```

```
                        85                    90                    95
agc caa gtc ccc acc gaa ccc aag aaa cta gag gag aat gag gtt atc        336
Ser Gln Val Pro Thr Glu Pro Lys Lys Leu Glu Glu Asn Glu Val Ile
                100                 105                 110 ccc aag aga atc tca ccc gtt gct aat tac aag aag ccc aaa ctc ctc        384
Pro Lys Arg Ile Ser Pro Val Ala Asn Tyr Lys Lys Pro Lys Leu Leu
            115                 120                 125 tac tgt agc aac ggg ggc cac ttc ctg agg atc ctt ccg gat ggc aca        432
Tyr Cys Ser Asn Gly Gly His Phe Leu Arg Ile Leu Pro Asp Gly Thr
        130                 135                 140 gtg gat ggg aca agg gac agg agc gac cag cac att cag ctc cag ctc        480
Val Asp Gly Thr Arg Asp Arg Ser Asp Gln His Ile Gln Leu Gln Leu
145                 150                 155                 160 agt gcg gaa agc gtg ggg gag gtg tat ata aag agt acc gag act ggc        528
Ser Ala Glu Ser Val Gly Glu Val Tyr Ile Lys Ser Thr Glu Thr Gly
                165                 170                 175 cag tac ttg gcc atg gac acc gac ggg ctt tta tac ggc tca cag aca        576
Gln Tyr Leu Ala Met Asp Thr Asp Gly Leu Leu Tyr Gly Ser Gln Thr
            180                 185                 190 cca aat gag gaa tgt ttg ttc ctg gaa agg ctg gag gag aac cat tac        624
Pro Asn Glu Glu Cys Leu Phe Leu Glu Arg Leu Glu Glu Asn His Tyr
        195                 200                 205 aac acc tat ata tcc aag aag cat gca gag aag aat tgg ttt gtt ggc        672
Asn Thr Tyr Ile Ser Lys Lys His Ala Glu Lys Asn Trp Phe Val Gly
    210                 215                 220 ctc aag aag aat ggg agc tgc aaa cgc ggt cct cgg act cac tat ggc        720
Leu Lys Lys Asn Gly Ser Cys Lys Arg Gly Pro Arg Thr His Tyr Gly
225                 230                 235                 240 cag aaa gca atc ttg ttt ctc ccc ctg cca gtc tct tct gat              762
Gln Lys Ala Ile Leu Phe Leu Pro Leu Pro Val Ser Ser Asp
                245                 250

<210> SEQ ID NO 23
<211> LENGTH: 281
<212> TYPE: PRT
<213> ORGANISM: Artificial Sequence
<220> FEATURE:
<223> OTHER INFORMATION: Description of Artificial Sequence: fusion of

<400> SEQUENCE: 23

Met Ala Pro Ala Arg Leu Phe Ala Leu Leu Leu Phe Phe Val Gly Gly
1               5                   10                  15

Val Ala Glu Ser Ile Arg Glu Thr Glu Val Ile Asp Pro Gln Asp Leu
            20                  25                  30

Leu Glu Gly Arg Tyr Phe Ser Gly Ala Leu Pro Asp Asp Glu Asp Val
        35                  40                  45

Val Gly Pro Gly Gln Glu Ser Asp Asp Phe Glu Leu Ser Gly Ser Gly
    50                  55                  60

Asp Leu Asp Asp Leu Glu Asp Ser Met Ile Gly Pro Glu Val Val His
65                  70                  75                  80

Pro Leu Val Pro Leu Asp Asn His Ile Pro Glu Arg Ala Gly Ser Gly
                85                  90                  95

Ser Gln Val Pro Thr Glu Pro Lys Lys Leu Glu Glu Asn Glu Val Ile
            100                 105                 110

Pro Lys Arg Ile Ser Pro Val Glu Glu Ser Glu Asp Val Ser Asn Lys
        115                 120                 125

Val Ser Met Ser Ser Thr Val Gln Gly Ser Asn Ile Phe Glu Arg Thr
    130                 135                 140
```

```
Glu Val Ala Asn Tyr Lys Lys Pro Lys Leu Leu Tyr Cys Ser Asn Gly
145                 150                 155                 160

Gly His Phe Leu Arg Ile Leu Pro Asp Gly Thr Val Asp Gly Thr Arg
                165                 170                 175

Asp Arg Ser Asp Gln His Ile Gln Leu Gln Leu Ser Ala Glu Ser Val
            180                 185                 190

Gly Glu Val Tyr Ile Lys Ser Thr Glu Thr Gly Gln Tyr Leu Ala Met
        195                 200                 205

Asp Thr Asp Gly Leu Leu Tyr Gly Ser Gln Thr Pro Asn Glu Glu Cys
    210                 215                 220

Leu Phe Leu Glu Arg Leu Glu Glu Asn His Tyr Asn Thr Tyr Ile Ser
225                 230                 235                 240

Lys Lys His Ala Glu Lys Asn Trp Phe Val Gly Leu Lys Lys Asn Gly
                245                 250                 255

Ser Cys Lys Arg Gly Pro Arg Thr His Tyr Gly Gln Lys Ala Ile Leu
            260                 265                 270

Phe Leu Pro Leu Pro Val Ser Ser Asp
        275                 280

<210> SEQ ID NO 24
<211> LENGTH: 843
<212> TYPE: DNA
<213> ORGANISM: Artificial Sequence
<220> FEATURE:
<223> OTHER INFORMATION: Description of Artificial Sequence: fusion of
      sequence for a part of human ryudocan and a part of human
      fibroblast growth factor 1
<220> FEATURE:
<221> NAME/KEY: CDS
<222> LOCATION: (1)..(843)

<400> SEQUENCE: 24 atg gcc ccc gcc cgt ctg ttc gcg ctg ctg ctg ttc ttc gta ggc gga      48
Met Ala Pro Ala Arg Leu Phe Ala Leu Leu Leu Phe Phe Val Gly Gly
1               5                   10                  15 gtc gcc gag tcg atc cga gag act gag gtc atc gac ccc cag gac ctc      96
Val Ala Glu Ser Ile Arg Glu Thr Glu Val Ile Asp Pro Gln Asp Leu
                20                  25                  30 cta gaa ggc cga tac ttc tcc gga gcc cta cca gac gat gag gat gta     144
Leu Glu Gly Arg Tyr Phe Ser Gly Ala Leu Pro Asp Asp Glu Asp Val
            35                  40                  45 gtg ggg ccc ggg cag gaa tct gat gac ttt gag ctg tct ggc tct gga     192
Val Gly Pro Gly Gln Glu Ser Asp Asp Phe Glu Leu Ser Gly Ser Gly
        50                  55                  60 gat ctg gat gac ttg gaa gac tcc atg atc ggc cct gaa gtt gtc cat     240
Asp Leu Asp Asp Leu Glu Asp Ser Met Ile Gly Pro Glu Val Val His
65                  70                  75                  80 ccc ttg gtg cct cta gat aac cat atc cct gag agg gca ggg tct ggg     288
Pro Leu Val Pro Leu Asp Asn His Ile Pro Glu Arg Ala Gly Ser Gly
                85                  90                  95 agc caa gtc ccc acc gaa ccc aag aaa cta gag gag aat gag gtt atc     336
Ser Gln Val Pro Thr Glu Pro Lys Lys Leu Glu Glu Asn Glu Val Ile
                100                 105                 110 ccc aag aga atc tca ccc gtt gaa gag agt gag gat gtg tcc aac aag     384
Pro Lys Arg Ile Ser Pro Val Glu Glu Ser Glu Asp Val Ser Asn Lys
            115                 120                 125 gtg tca atg tcc agc act gtg cag ggc agc aac atc ttt gag aga acg     432
Val Ser Met Ser Ser Thr Val Gln Gly Ser Asn Ile Phe Glu Arg Thr
        130                 135                 140 gag gtc gct aat tac aag aag ccc aaa ctc ctc tac tgt agc aac ggg     480
Glu Val Ala Asn Tyr Lys Lys Pro Lys Leu Leu Tyr Cys Ser Asn Gly
```

```
Glu Val Ala Asn Tyr Lys Lys Pro Lys Leu Leu Tyr Cys Ser Asn Gly
145                 150                 155                 160 ggc cac ttc ctg agg atc ctt ccg gat ggc aca gtg gat ggg aca agg       528
Gly His Phe Leu Arg Ile Leu Pro Asp Gly Thr Val Asp Gly Thr Arg
                165                 170                 175 gac agg agc gac cag cac att cag ctg cag ctc agt gcg gaa agc gtg       576
Asp Arg Ser Asp Gln His Ile Gln Leu Gln Leu Ser Ala Glu Ser Val
            180                 185                 190 ggg gag gtg tat ata aag agt acc gag act ggc cag tac ttg gcc atg       624
Gly Glu Val Tyr Ile Lys Ser Thr Glu Thr Gly Gln Tyr Leu Ala Met
        195                 200                 205 gac acc gac ggg ctt tta tac ggc tca cag aca cca aat gag gaa tgt       672
Asp Thr Asp Gly Leu Leu Tyr Gly Ser Gln Thr Pro Asn Glu Glu Cys
    210                 215                 220 ttg ttc ctg gaa agg ctg gag gag aac cat tac aac acc tat ata tcc       720
Leu Phe Leu Glu Arg Leu Glu Glu Asn His Tyr Asn Thr Tyr Ile Ser
225                 230                 235                 240 aag aag cat gca gag aag aat tgg ttt gtt ggc ctc aag aag aat ggg       768
Lys Lys His Ala Glu Lys Asn Trp Phe Val Gly Leu Lys Lys Asn Gly
                245                 250                 255 agc tgc aaa cgc ggt cct cgg act cac tat ggc cag aaa gca atc ttg       816
Ser Cys Lys Arg Gly Pro Arg Thr His Tyr Gly Gln Lys Ala Ile Leu
            260                 265                 270 ttt ctc ccc ctg cca gtc tct tct gat                                   843
Phe Leu Pro Leu Pro Val Ser Ser Asp
        275                 280

<210> SEQ ID NO 25
<211> LENGTH: 172
<212> TYPE: PRT
<213> ORGANISM: Artificial Sequence
<220> FEATURE:
<223> OTHER INFORMATION: Description of Artificial Sequence: fusion of
      sequence for a part of mouse fibroblast growth factor 6 and
      a part of human fibroblast growth factor 1

<400> SEQUENCE: 25

Met Ser Arg Gly Ala Gly Arg Val Gln Gly Thr Leu Gln Ala Leu Val
1               5                   10                  15

Phe Leu Gly Val Leu Val Gly Met Val Val Pro Ser Pro Ala Gly Ala
            20                  25                  30

Arg Ala Asn Gly Ser Ala Asn Tyr Lys Lys Pro Lys Leu Leu Tyr Cys
        35                  40                  45

Ser Asn Gly Gly His Phe Leu Arg Ile Leu Pro Asp Gly Thr Val Asp
    50                  55                  60

Gly Thr Arg Asp Arg Ser Asp Gln His Ile Gln Leu Gln Leu Ser Ala
65                  70                  75                  80

Glu Ser Val Gly Glu Val Tyr Ile Lys Ser Thr Glu Thr Gly Gln Tyr
                85                  90                  95

Leu Ala Met Asp Thr Asp Gly Leu Leu Tyr Gly Ser Gln Thr Pro Asn
            100                 105                 110

Glu Glu Cys Leu Phe Leu Glu Arg Leu Glu Glu Asn His Tyr Asn Thr
        115                 120                 125

Tyr Ile Ser Lys Lys His Ala Glu Lys Asn Trp Phe Val Gly Leu Lys
    130                 135                 140

Lys Asn Gly Ser Cys Lys Arg Gly Pro Arg Thr His Tyr Gly Gln Lys
145                 150                 155                 160

Ala Ile Leu Phe Leu Pro Leu Pro Val Ser Ser Asp
                165                 170
```

-continued

<210> SEQ ID NO 26
<211> LENGTH: 516
<212> TYPE: DNA
<213> ORGANISM: Artificial Sequence
<220> FEATURE:
<223> OTHER INFORMATION: Description of Artificial Sequence: fusion of
      sequence for a part of mouse fibroblast growth factor 6 and
      a part of human fibroblast growth factor 1
<220> FEATURE:
<221> NAME/KEY: CDS
<222> LOCATION: (1)..(516)

<400> SEQUENCE: 26

```
atg tcc cgg gga gca gga cgt gtt cag ggc acg ctg cag gct ctc gtc        48
Met Ser Arg Gly Ala Gly Arg Val Gln Gly Thr Leu Gln Ala Leu Val
1               5                   10                  15 ttc tta ggc gtc cta gtg ggc atg gtg gtg ccc tca cct gcc ggc gcc        96
Phe Leu Gly Val Leu Val Gly Met Val Val Pro Ser Pro Ala Gly Ala
                20                  25                  30 cgc gcc aac ggc tcg gct aat tac aag aag ccc aaa ctc ctc tac tgt       144
Arg Ala Asn Gly Ser Ala Asn Tyr Lys Lys Pro Lys Leu Leu Tyr Cys
            35                  40                  45 agc aac ggg ggc cac ttc ctg agg atc ctt ccg gat ggc aca gtg gat       192
Ser Asn Gly Gly His Phe Leu Arg Ile Leu Pro Asp Gly Thr Val Asp
        50                  55                  60 ggg aca agg gac agg agc gac cag cac att cag ctg cag ctc agt gcg       240
Gly Thr Arg Asp Arg Ser Asp Gln His Ile Gln Leu Gln Leu Ser Ala
65                  70                  75                  80 gaa agc gtg ggg gag gtg tat ata aag agt acc gag act ggc cag tac       288
Glu Ser Val Gly Glu Val Tyr Ile Lys Ser Thr Glu Thr Gly Gln Tyr
                85                  90                  95 ttg gcc atg gac acc gac ggg ctt tta tac ggc tca cag aca cca aat       336
Leu Ala Met Asp Thr Asp Gly Leu Leu Tyr Gly Ser Gln Thr Pro Asn
                100                 105                 110 gag gaa tgt ttg ttc ctg gaa agg ctg gag gag aac cat tac aac acc       384
Glu Glu Cys Leu Phe Leu Glu Arg Leu Glu Glu Asn His Tyr Asn Thr
            115                 120                 125 tat ata tcc aag aag cat gca gag aag aat tgg ttt gtt ggc ctc aag       432
Tyr Ile Ser Lys Lys His Ala Glu Lys Asn Trp Phe Val Gly Leu Lys
        130                 135                 140 aag aat ggg agc tgc aaa cgc ggt cct cgg act cac tat ggc cag aaa       480
Lys Asn Gly Ser Cys Lys Arg Gly Pro Arg Thr His Tyr Gly Gln Lys
145                 150                 155                 160 gca atc ttg ttt ctc ccc ctg cca gtc tct tct gat                       516
Ala Ile Leu Phe Leu Pro Leu Pro Val Ser Ser Asp
                165                 170
```

<210> SEQ ID NO 27
<211> LENGTH: 210
<212> TYPE: PRT
<213> ORGANISM: Artificial Sequence
<220> FEATURE:
<223> OTHER INFORMATION: Description of Artificial Sequence: fusion of
      sequence for a part of mouse fibroblast growth factor 6 and
      a part of human fibroblast growth 1

<400> SEQUENCE: 27

```
Met Ser Arg Gly Ala Gly Arg Val Gln Gly Thr Leu Gln Ala Leu Val
1               5                   10                  15

Phe Leu Gly Val Leu Val Gly Met Val Val Pro Ser Pro Ala Gly Ala
                20                  25                  30

Arg Ala Asn Gly Thr Leu Leu Asp Ser Arg Gly Trp Gly Thr Leu Leu
```

```
                35                  40                  45
Ser Arg Ser Arg Ala Gly Leu Ala Gly Glu Ile Ser Gly Val Asn Trp
 50                  55                  60

Glu Ser Gly Tyr Leu Val Gly Ile Lys Arg Gln Ala Asn Tyr Lys Lys
 65                  70                  75                  80

Pro Lys Leu Leu Tyr Cys Ser Asn Gly Gly His Phe Leu Arg Ile Leu
                 85                  90                  95

Pro Asp Gly Thr Val Asp Gly Thr Arg Asp Arg Ser Asp Gln His Ile
            100                 105                 110

Gln Leu Gln Leu Ser Ala Glu Ser Val Gly Glu Val Tyr Ile Lys Ser
        115                 120                 125

Thr Glu Thr Gly Gln Tyr Leu Ala Met Asp Thr Asp Gly Leu Leu Tyr
    130                 135                 140

Gly Ser Gln Thr Pro Asn Glu Glu Cys Leu Phe Leu Glu Arg Leu Glu
145                 150                 155                 160

Glu Asn His Tyr Asn Thr Tyr Ile Ser Lys Lys His Ala Glu Lys Asn
                165                 170                 175

Trp Phe Val Gly Leu Lys Lys Asn Gly Ser Cys Lys Arg Gly Pro Arg
            180                 185                 190

Thr His Tyr Gly Gln Lys Ala Ile Leu Phe Leu Pro Leu Pro Val Ser
        195                 200                 205

Ser Asp
    210

<210> SEQ ID NO 28
<211> LENGTH: 630
<212> TYPE: DNA
<213> ORGANISM: Artificial Sequence
<220> FEATURE:
<223> OTHER INFORMATION: Description of Artificial Sequence: fusion of
      sequence for a part of mouse fibroblast growth factor 6 and
      a part of human fibroblast growth 1
<220> FEATURE:
<221> NAME/KEY: CDS
<222> LOCATION: (1)..(630)

<400> SEQUENCE: 28 atg tcc cgg gga gca gga cgt gtt cag ggc acg ctg cag gct ctc gtc      48
Met Ser Arg Gly Ala Gly Arg Val Gln Gly Thr Leu Gln Ala Leu Val
 1               5                  10                  15 ttc tta ggc gtc cta gtg ggc atg gtg gtg ccc tca cct gcc ggc gcc      96
Phe Leu Gly Val Leu Val Gly Met Val Val Pro Ser Pro Ala Gly Ala
             20                  25                  30 cgc gcc aac ggc acg cta ctg gac tcc aga ggc tgg ggc acc ctc ttg     144
Arg Ala Asn Gly Thr Leu Leu Asp Ser Arg Gly Trp Gly Thr Leu Leu
         35                  40                  45 tcc agg tct cga gct ggg cta gct gga gag att tcg ggt gtg aat tgg     192
Ser Arg Ser Arg Ala Gly Leu Ala Gly Glu Ile Ser Gly Val Asn Trp
 50                  55                  60 gaa agc ggc tat ttg gtg ggc att aag cga cag gct aat tac aag aag     240
Glu Ser Gly Tyr Leu Val Gly Ile Lys Arg Gln Ala Asn Tyr Lys Lys
 65                  70                  75                  80 ccc aaa ctc ctc tac tgt agc aac ggg ggc cac ttc ctg agg atc ctt     288
Pro Lys Leu Leu Tyr Cys Ser Asn Gly Gly His Phe Leu Arg Ile Leu
                 85                  90                  95 ccg gat ggc aca gtg gat ggg aca agg gac agg agc gac cag cac att     336
Pro Asp Gly Thr Val Asp Gly Thr Arg Asp Arg Ser Asp Gln His Ile
            100                 105                 110 cag ctg cag ctc agt gcg gaa agc gtg ggg gag gtg tat ata aag agt     384
Gln Leu Gln Leu Ser Ala Glu Ser Val Gly Glu Val Tyr Ile Lys Ser
```

```
                Gln Leu Gln Leu Ser Ala Glu Ser Val Gly Glu Val Tyr Ile Lys Ser
                        115                 120                 125 acc gag act ggc cag tac ttg gcc atg gac acc gac ggg ctt tta tac        432
Thr Glu Thr Gly Gln Tyr Leu Ala Met Asp Thr Asp Gly Leu Leu Tyr
130                 135                 140 ggc tca cag aca cca aat gag gaa tgt ttg ttc ctg gaa agg ctg gag        480
Gly Ser Gln Thr Pro Asn Glu Glu Cys Leu Phe Leu Glu Arg Leu Glu
145                 150                 155                 160 gag aac cat tac aac acc tat ata tcc aag aag cat gca gag aag aat        528
Glu Asn His Tyr Asn Thr Tyr Ile Ser Lys Lys His Ala Glu Lys Asn
                165                 170                 175 tgg ttt gtt ggc ctc aag aag aat ggg agc tgc aaa cgc ggt cct cgg        576
Trp Phe Val Gly Leu Lys Lys Asn Gly Ser Cys Lys Arg Gly Pro Arg
                180                 185                 190 act cac tat ggc cag aaa gca atc ttg ttt ctc ccc ctg cca gtc tct        624
Thr His Tyr Gly Gln Lys Ala Ile Leu Phe Leu Pro Leu Pro Val Ser
            195                 200                 205 tct gat                                                                630
Ser Asp
    210
```

<210> SEQ ID NO 29
<211> LENGTH: 180
<212> TYPE: PRT
<213> ORGANISM: Artificial Sequence
<220> FEATURE:
<223> OTHER INFORMATION: Description of Artificial Sequence: fusion of
      sequence for a part of mouse fibroblast growth factor 6,
      a part of human fibroblast growth factor 1 and an artificial
      sequence

<400> SEQUENCE: 29

```
Met Ser Arg Gly Ala Gly Arg Val Gln Gly Thr Leu Gln Ala Leu Val
 1               5                  10                  15

Phe Leu Gly Val Leu Val Gly Met Val Val Pro Ser Pro Ala Gly Ala
                20                  25                  30

Arg Ala Asn Gly Thr Leu Leu Asp Ala Asn Tyr Lys Lys Pro Lys Leu
            35                  40                  45

Leu Tyr Cys Ser Asn Gly Gly His Phe Leu Arg Ile Leu Pro Asp Gly
        50                  55                  60

Thr Val Asp Gly Thr Arg Asp Arg Ser Asp Gln His Ile Gln Leu Gln
65                  70                  75                  80

Leu Ser Ala Glu Ser Val Gly Glu Val Tyr Ile Lys Ser Thr Glu Thr
                85                  90                  95

Gly Gln Tyr Leu Ala Met Asp Thr Asp Gly Leu Leu Tyr Gly Ser Gln
                100                 105                 110

Thr Pro Asn Glu Glu Cys Leu Phe Leu Glu Arg Leu Glu Glu Asn Ala
            115                 120                 125

Thr Pro Ala Pro His Tyr Asn Thr Tyr Ile Ser Lys Lys His Ala Glu
        130                 135                 140

Lys Asn Trp Phe Val Gly Leu Lys Lys Asn Gly Ser Cys Lys Arg Gly
145                 150                 155                 160

Pro Arg Thr His Tyr Gly Gln Lys Ala Ile Leu Phe Leu Pro Leu Pro
                165                 170                 175

Val Ser Ser Asp
            180
```

<210> SEQ ID NO 30
<211> LENGTH: 540

<212> TYPE: DNA
<213> ORGANISM: Artificial Sequence
<220> FEATURE:
<223> OTHER INFORMATION: Description of Artificial Sequence: fusion of
      sequence for a part of mouse fibroblast growth factor 6,
      a part of human fibroblast growth factor 1 and an artificial
      sequence
<220> FEATURE:
<221> NAME/KEY: CDS
<222> LOCATION: (1)..(540)

<400> SEQUENCE: 30

| atg | tcc | cgg | gga | gca | gga | cgt | gtt | cag | ggc | acg | ctg | cag | gct | ctc | gtc | 48 |
| Met | Ser | Arg | Gly | Ala | Gly | Arg | Val | Gln | Gly | Thr | Leu | Gln | Ala | Leu | Val | |
| 1   |     |     |     | 5   |     |     |     |     | 10  |     |     |     |     | 15  |     | |

| ttc | tta | ggc | gtc | cta | gtg | ggc | atg | gtg | gtg | ccc | tca | cct | gcc | ggc | gcc | 96 |
| Phe | Leu | Gly | Val | Leu | Val | Gly | Met | Val | Val | Pro | Ser | Pro | Ala | Gly | Ala | |
|     |     |     | 20  |     |     |     |     | 25  |     |     |     |     | 30  |     |     | |

| cgc | gcc | aac | ggc | acg | cta | ctg | gac | gct | aat | tac | aag | aag | ccc | aaa | ctc | 144 |
| Arg | Ala | Asn | Gly | Thr | Leu | Leu | Asp | Ala | Asn | Tyr | Lys | Lys | Pro | Lys | Leu | |
|     | 35  |     |     |     |     | 40  |     |     |     |     | 45  |     |     |     |     | |

| ctc | tac | tgt | agc | aac | ggg | ggc | cac | ttc | ctg | agg | atc | ctt | ccg | gat | ggc | 192 |
| Leu | Tyr | Cys | Ser | Asn | Gly | Gly | His | Phe | Leu | Arg | Ile | Leu | Pro | Asp | Gly | |
|     | 50  |     |     |     |     | 55  |     |     |     |     | 60  |     |     |     |     | |

| aca | gtg | gat | ggg | aca | agg | gac | agg | agc | gac | cag | cac | att | cag | ctg | cag | 240 |
| Thr | Val | Asp | Gly | Thr | Arg | Asp | Arg | Ser | Asp | Gln | His | Ile | Gln | Leu | Gln | |
| 65  |     |     |     |     | 70  |     |     |     |     | 75  |     |     |     |     | 80  | |

| ctc | agt | gcg | gaa | agc | gtg | ggg | gag | gtg | tat | ata | aag | agt | acc | gag | act | 288 |
| Leu | Ser | Ala | Glu | Ser | Val | Gly | Glu | Val | Tyr | Ile | Lys | Ser | Thr | Glu | Thr | |
|     |     |     |     | 85  |     |     |     |     | 90  |     |     |     |     | 95  |     | |

| ggc | cag | tac | ttg | gcc | atg | gac | acc | gac | ggg | ctt | tta | tac | ggc | tca | cag | 336 |
| Gly | Gln | Tyr | Leu | Ala | Met | Asp | Thr | Asp | Gly | Leu | Leu | Tyr | Gly | Ser | Gln | |
|     |     |     | 100 |     |     |     |     | 105 |     |     |     |     | 110 |     |     | |

| aca | cca | aat | gag | gaa | tgt | ttg | ttc | ctg | gaa | agg | ctg | gag | gag | aac | gct | 384 |
| Thr | Pro | Asn | Glu | Glu | Cys | Leu | Phe | Leu | Glu | Arg | Leu | Glu | Glu | Asn | Ala | |
|     |     | 115 |     |     |     |     | 120 |     |     |     |     | 125 |     |     |     | |

| act | cca | gct | cca | cat | tac | aac | acc | tat | ata | tcc | aag | aag | cat | gca | gag | 432 |
| Thr | Pro | Ala | Pro | His | Tyr | Asn | Thr | Tyr | Ile | Ser | Lys | Lys | His | Ala | Glu | |
|     | 130 |     |     |     |     | 135 |     |     |     |     | 140 |     |     |     |     | |

| aag | aat | tgg | ttt | gtt | ggc | ctc | aag | aag | aat | ggg | agc | tgc | aaa | cgc | ggt | 480 |
| Lys | Asn | Trp | Phe | Val | Gly | Leu | Lys | Lys | Asn | Gly | Ser | Cys | Lys | Arg | Gly | |
| 145 |     |     |     |     | 150 |     |     |     |     | 155 |     |     |     |     | 160 | |

| cct | cgg | act | cac | tat | ggc | cag | aaa | gca | atc | ttg | ttt | ctc | ccc | ctg | cca | 528 |
| Pro | Arg | Thr | His | Tyr | Gly | Gln | Lys | Ala | Ile | Leu | Phe | Leu | Pro | Leu | Pro | |
|     |     |     |     | 165 |     |     |     |     | 170 |     |     |     |     | 175 |     | |

| gtc | tct | tct | gat | | | | | | | | | | | | | 540 |
| Val | Ser | Ser | Asp | | | | | | | | | | | | | |
|     |     |     | 180 | | | | | | | | | | | | | |

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:primer for
      PCR

<400> SEQUENCE: 31
aacaaaagct gggtaccggg                                             20

HEPARIN-BINDING PROTEINS MODIFIED WITH SUGAR CHAINS, METHOD OF PRODUCING THE SAME AND PHARMACEUTICAL COMPOSITIONS CONTAINING SAME

CROSS REFERENCE TO RELATED APPLICATION

This application is a divisional of U.S. patent application Ser. No. 09/121,017, filed Jul. 22, 1998, now U.S. Pat. No. 7,005,415.

BACKGROUND OF THE INVENTION

The present invention relates to a heparin-binding protein functionalized by covalently bonding thereto a sugar chain, a method for producing the protein and a pharmaceutical composition containing the protein.

It has been known that heparin-binding proteins, among all, those proteins classified into the fibroblast growth factor (hereinafter, referred to as "FGF") family and fibroblast growth factor homologous factors strongly bind to heparin and heparan sulfate (sulfated polysaccharides) by a non-covalent bond. It has been also known that when a heparin-binding protein such as fibroblast growth factor is mixed with a sulfated polysaccharide such as heparin, the biological activity and physical properties of the heparin-binding protein are altered to change its function; sometimes, such a heparin-binding protein may acquire higher function. However, even if a sulfated polysaccharide was mixed with, the expected functionalization of the protein has been limited. Besides, when such a mixture is used as a pharmaceutical composition, unfavorable physiological activity attributable to a free sulfated polysaccharide has caused a problem. To date, there has been reported no protein in which a heparin-binding protein is joined with a sulfated polysaccharide by a covalent bond for the purpose of functionalization of the heparin-binding protein.

In addition, it has never been known to date that artificial addition of an asparagine-linked sugar chain (hereinafter, referred to as an "N-linked sugar chain") or serine/threonine-linked sugar chain (hereinafter, referred to as an "O-linked sugar chain") to a heparin-binding protein, particularly a protein of the FGF family or a fibroblast growth factor homologous factor, by a covalent bond can functionalize the protein. Furthermore, the general effect which an N-linked sugar chain or O-linked sugar chain could give has not been known. Exceptionally, with respect to FGF-6, the role of the N-linked sugar chain it naturally has was suggested in an in vitro translation system, but has not been proved directly. To date, there has been reported no example of joining a heparin-binding protein with an N-linked or O-linked sugar chain by a covalent bond for the purpose of functionalizing the heparin-binding protein.

It is an object of the present invention to improve the function of heparin-binding proteins. It is another object of the invention to establish a heparin-binding protein to which a sugar chain is covalently bonded and a method for producing the protein. It is still another object of the invention to provide a pharmaceutical composition containing the above protein.

SUMMARY OF THE INVENTION

The present inventors have made intensive and extensive researches toward the solution of the above problems. As a result, the inventors have noted the fact that a sulfated polysaccharide, a glycosaminoglycan, an N-linked sugar chain and an O-linked sugar chain are individually synthesized in living animal bodies as a sugar chain of a glycoprotein. Then, the inventors have found that it is possible to produce a heparin-binding protein having in its molecule a sulfated polysaccharide, a glycosaminoglycan, an N-linked sugar chain or an O-linked sugar chain covalently bonded thereto by ensuring that a cDNA coding for a peptide to which any of the above sugar chains can be added is ligated to a cDNA coding for the heparin-binding protein, and by then allowing an animal cell to produce the gene product of the ligated cDNA. Furthermore, the inventors have confirmed that the function of the resultant sugar chain-added heparin-binding protein is improved. Thus, the present invention has been achieved based on these findings.

The present invention provides a heparin-binding protein functionalized by covalently bonding thereto a sugar chain. The sugar chain may be selected from the group consisting of a sulfated polysaccharide, a glycosaminoglycan, an N-linked sugar chain, an O-linked sugar chain and a combination thereof. The heparin-binding protein may be a factor belonging to the FGF family or its allied factor. The heparin-binding protein may be covalently bonded to the sugar chain through a peptide to which the sugar chain can be added. For example, the heparin-binding protein to which the sugar chain is to be covalently bonded may be the following (a) or (b):

(a) a protein consisting of the amino acid sequence of SEQ ID NO: 1, 3, 5, 17, 19, 21, 23, 25, 27 or 29;

(b) a protein which consists of the amino acid sequence of SEQ ID NO: 1, 3, 5, 17, 19, 21, 23, 25, 27 or 29 having deletion, substitution, addition or modification of one or several amino acids, which has FGF activity and to which the sugar chain can be added.

In the heparin-binding protein of the invention, the sugar chain may be bonded to the heparin-binding protein at a site forming a turn in the secondary structure or a site near one of the ends, or a site which would not change the tertiary structure of the protein greatly by addition of the sugar chain.

The present invention also provides a method for producing a heparin-binding protein functionalized by covalently bonding thereto a sugar chain, comprising the following steps:

(a) a step in which a cDNA coding for a peptide to which a sugar chain can be added is ligated to a cDNA coding for a heparin-binding protein;

(b) a step of incorporating the resultant ligated cDNA into an expression vector;

(c) a step of introducing the expression vector into a host cell having a sugar chain addition pathway; and (d) a step of expressing in the host cell a heparin-binding protein to which a sugar chain is covalently bonded through the peptide to which the sugar chain can be added.

When the sugar chain is a sulfated polysaccharide or a glycosaminoglycan, the peptide to which the sugar chain can be added may be a proteoglycan core protein or a part thereof. When the sugar chain is an N-linked sugar chain, the peptide to which the sugar chain can be added may be a peptide comprising an N-linked sugar chain-added amino acid sequence. When the sugar chain is an O-linked sugar chain, the peptide to which the sugar chain can be added may be a peptide comprising an O-linked sugar chain-added amino acid sequence. The present invention also provides a method for producing a heparin-binding protein functionalized by covalently bonding thereto a sugar chain, comprising a step of allowing the sugar chain to bind to the heparin-binding protein by a chemical binding method. The sugar chain may be selected from the group consisting of a sulfated polysaccharide, a glycosaminoglycan, an N-linked sugar chain, an O-linked sugar chain and a combination thereof, and the heparin-binding protein may be a factor belonging to the FGF family or its allied factor. The present invention further provides a pharmaceutical composition containing, as an active ingredient, a heparin-binding protein functionalized by covalently bonding thereto a sugar chain. The present invention also provides a method for functionalizing a natural protein having no sugar chain by covalently bonding thereto a sugar chain.

The novel sugar chain-added heparin-binding protein of the invention is excellent in stabilities such as thermostability, acid resistance, alkali resistance and resistance to proteolytic enzymes. Thus, by using the sugar chain-added heparin-binding protein of the invention in a pharmaceutical product, it is possible to design such a pharmaceutical product that is excellent in in vivo stabilities, in particular acid resistance and alkali resistance, and applicable to an oral medicine.

BRIEF DESCRIPTION OF THE DRAWINGS

FIG. 5 shows the DNA synthesis promoting activity on HUVEC of S/FGF-1a-II and *E. coli*-derived FGF-1a.

FIG. 6 shows the thermostability, acid resistance and alkali resistance of S/FGF-1a-II and *E. coli*-derived FGF-1a.

FIG. 7 shows the resistance to trypsin of S/FGF-1a-II and *E. coli*-derived FGF-1a.

FIG. 8 shows the DNA synthesis promoting activity on HUVEC of N-FGF-6/1a-IV and *E. coli*-derived FGF-1a.

DESCRIPTION OF PREFERRED EMBODIMENTS

Figure 1:
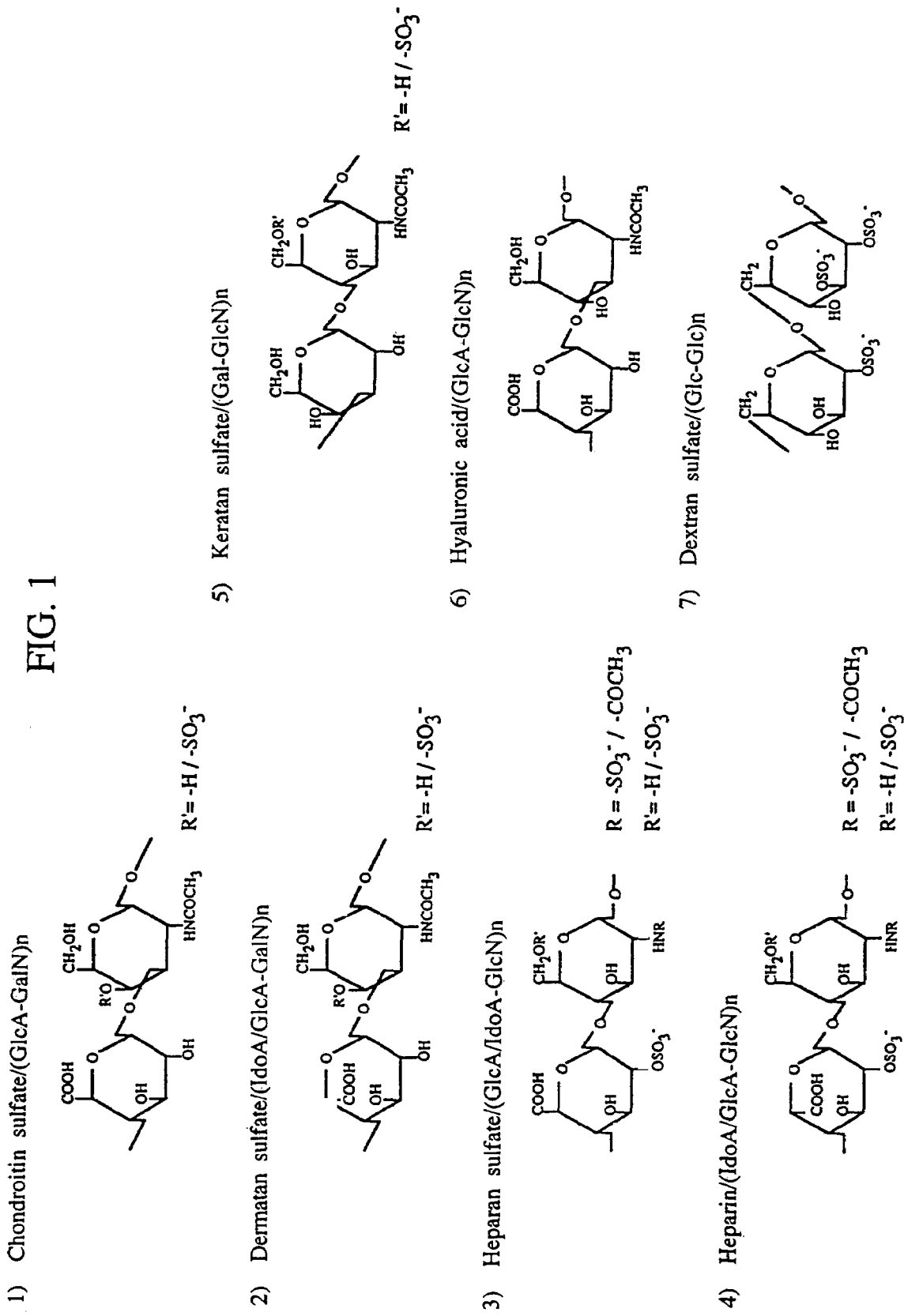
FIG. 1 shows typical examples of sulfated polysaccharide and glycosaminoglycan sugar chains.

Hereinbelow, the present invention will be described in detail.

In the present invention, the heparin-binding protein to which a sugar chain is to be covalently bonded is a protein having heparin binding property. For example, factors belonging to the FGF family or allied factors, or other proteins with heparin-binding property but without structural similarity to the former proteins may be enumerated. Examples of the other proteins include, but are not limited to, heparin-binding epidermal growth factor-like factor (HB-EGF) and platelet-derived growth factor (PDGF). As specific examples of the factors belonging to the FGF family or allied factors, FGF-1 to -10 and FHF (fibroblast growth factor homologous factor)-1 to -4 are known. The heparin-binding protein of the invention may be covalently bonded to a sugar chain through a peptide to which the sugar chain can be added. For example, the heparin-binding protein to which the sugar chain is to be covalently bonded may be the following (a) or (b):

(a) a protein consisting of the amino acid sequence of SEQ ID NO: 1, 3, 5, 17, 19, 21, 23, 25, 27 or 29;

(b) a protein which consists of the amino acid sequence of SEQ ID NO: 1, 3, 5, 17, 19, 21, 23, 25, 27 or 29 having deletion, substitution, addition or modification of one or several amino acids, which has FGF activity and to which the sugar chain can be added.

Proteins having the amino acid sequences of SEQ ID NOS: 1, 3, 5, 17, 19, 21, 23, 25, 27 and 29 are encoded by, for example, the DNA sequences of SEQ ID NOS: 2, 4, 6, 18, 20, 22, 24, 26, 28 and 30, respectively. These proteins contain a peptide sequence to which a sugar chain can be added and a sequence for a signal peptide in addition to a peptide sequence for a factor belonging to the FGF family. The heparin-binding protein of the present invention includes not only the protein primarily defined by a cDNA shown in the sequence listing but also a protein in which a peptide sequence for secretion (called the signal peptide) located at the amino terminal when secreted from cells is cut off. The utility of a heparin-binding protein which is contained in the pharmaceutical composition of the invention as an active ingredient will not vary even if the protein is produced in a form lacking the signal peptide from the beginning.

The sugar chain to be covalently bonded to the heparin-binding protein may be any sugar chain as long as the protein is functionalized by covalently bonding the sugar chain. Examples of the sugar chain include, but are not limited to, sulfated polysaccharides such as heparan sulfate, chondroitin sulfate, glycosaminoglycans, N-linked sugar chains and O-linked sugar chains. The term "functionalize" used herein means increasing the activity of a protein of interest. As an example of functionalization, there may be given a case in which the residual activity of a protein after treatment with heat, acid or alkali is increased by adding a sugar chain to the protein by a covalent bond. The "sulfated polysaccharide" used herein is a general term for various sugar chain structures which are elongating from xylose linked to a serine residue present in the primary structure of proteins or elongating on the non-reducing end side of N-linked sugar chains or O-linked sugar chains to be described later, or which are present in a free form.

Many of such sugar chains are composed of repeating disaccharides of aminosugar and uronic acid (or galactose), and some of their hydroxyl groups or amino groups are substituted with sulfate groups. Glycosaminoglycans are polysaccharides having a structure similar to those described above, but they include those which do not have any substitution with sulfate groups. All of the above-mentioned polysaccharides are designated herein generically "sulfated polysaccharides or the like".

Figure 2:
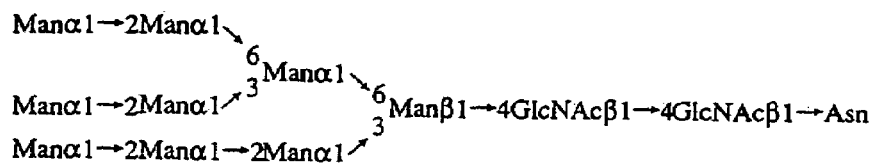
FIG. 2 shows typical examples of N-linked sugar chains.
Figure 2:
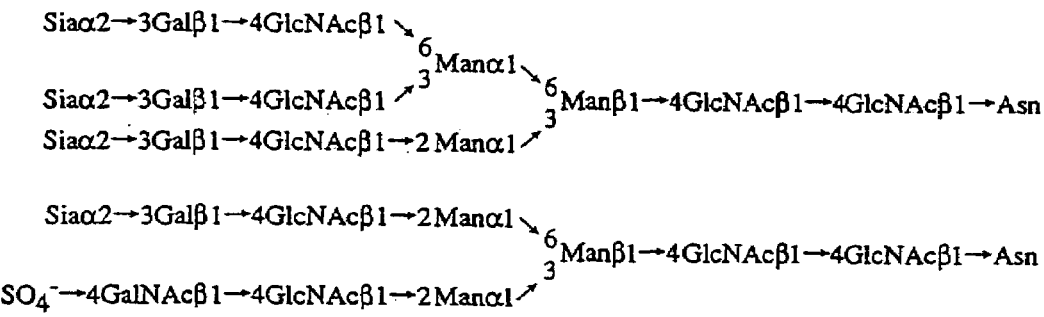
Figure 2:
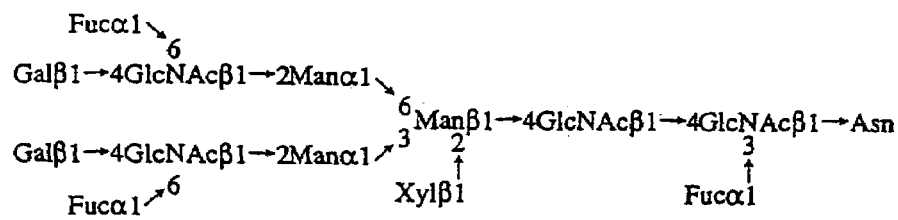
Figure 2:
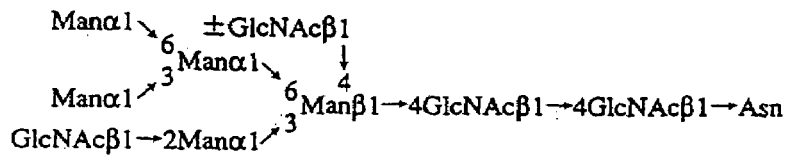
Figure 3:
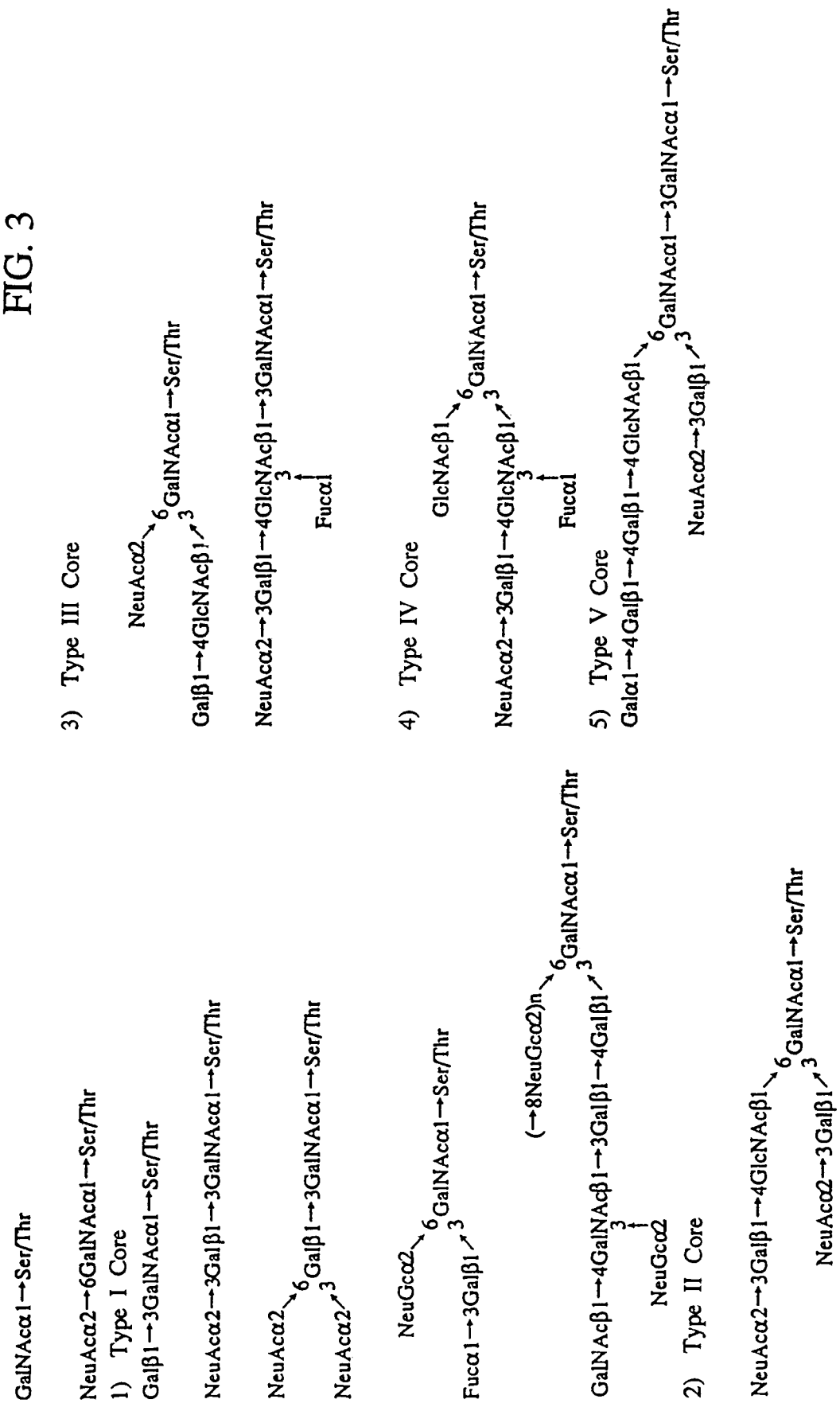
FIG. 3 shows typical examples of O-linked sugar chains.

Their specific structures are described, for example, in *Destiny of Sugar Chains in Cells*, Nagai, Hakomori and Kobata (Eds.), Kodansha Scientific Co. FIG. 1 shows their typical sugar chain sequences. The "N-linked sugar chain" used herein is a general term for various sugar chain structures elongating from N-acetylglucosamine linked to an asparagine residue present in the primary structure of proteins. Their specific structures are described, for example, in *Destiny of Sugar Chains in Cells*, Nagai, Hakomori and Kobata (Eds.), Kodansha Scientific Co. FIG. 2 shows their typical sugar chain sequences. The "O-linked sugar chain" used herein is a general term for various sugar chain structures elongating from N-acetylgalactosamine linked to a serine or threonine residue present in the primary structure of proteins. Their specific structures are described, for example, in *Destiny of Sugar Chains in Cells*, Nagai, Hakomori and Kobata (Eds.), Kodansha Scientific Co. FIG. 3 shows their typical sugar chain sequences. These sulfated polysaccharides or the like, N-linked sugar chains and O-linked sugar chains may have addition, deletion, substitution or modification in a part of their sugar chain sequences as long as they retain their functions.

When a sugar chain is attached to a heparin-binding protein, the sugar chain alone may be covalently bonded to the heparin-binding protein directly. Alternatively, a peptide chain of any length to which a sugar chain is covalently bonding may be covalently bonded to a heparin-binding protein.

In order to produce the heparin-binding protein of the invention to which a sugar chain is covalently bonded (hereinafter, referred to as the "sugar chain-added heparin-binding protein"), first, a cDNA coding for a peptide to which a sugar chain can be added is ligated to a cDNA coding for a heparin-binding protein. The ligated cDNA is incorporated into an appropriate expression vector, which is then introduced into a host cell having a sugar chain addition pathway to thereby express a sugar chain-added heparin-binding protein.

cDNAs coding for various heparin-binding proteins can be obtained by designing appropriate primers from a sequence registered in a gene bank such as DDBJ (DNA Data Bank of Japan) and performing RT-PCR (reverse transcription PCR) with the primers and mRNA from the relevant tissue of the relevant animal.

In order to produce a sulfated polysaccharide or the like-added heparin-binding protein, first, a cDNA coding for a heparin-binding protein is ligated to a cDNA coding for a peptide which is known to undergo addition of a sulfated polysaccharide or the like. The ligated cDNA is incorporated into an appropriate host cell expression vector, which is then introduced into a host cell to thereby express the sulfated polysaccharide or the like-added heparin-binding protein. As the peptide which is known to undergo addition of a sulfated polysaccharide or the like, the core protein or a part thereof of various proteoglycans (e.g. syndecan, glypican, perlecan) may be used. As a part of the core protein of a proteoglycan, a peptide comprising a Ser-Gly repeat sequence (which is believed to be the sugar chain addition site in proteoglycans) may be used.

In order to produce an N-linked sugar chain-added heparin-binding protein, first, a cDNA coding for a heparin-binding protein is ligated to a cDNA coding for a peptide which is known to undergo addition of an N-linked sugar chain. The ligated cDNA is incorporated into an appropriate host cell expression vector, which is then introduced into a host cell to thereby express the N-linked sugar chain-added heparin-binding protein. Specific examples of the peptide which is known to undergo addition of an N-linked sugar chain include Asn-X-Thr and Asn-X-Ser (wherein X is any amino acid except proline).

In order to produce an O-linked sugar chain-added heparin-binding protein, first, a cDNA coding for a heparin-binding protein is ligated to a cDNA coding for a peptide which is known to undergo addition of an O-linked sugar chain. The ligated cDNA is incorporated into an appropriate host cell expression vector, which is then introduced into a host cell to thereby express the O-linked sugar chain-added heparin-binding protein. As a specific examples of the peptide which is known to undergo addition of an O-linked sugar chain, Ala-Thr-Pro-Ala-Pro may be given.

As the site to which a sugar chain is bonded, a site forming a turn in the secondary structure of a heparin-binding protein or a site near one of the ends, or a site which would not change the tertiary structure of the protein greatly by addition of the sugar chain is preferable.

One example of the method for producing a sugar chain-added heparin-binding protein of the invention will be described below.

First, an oligonucleotide coding for a secretion signal and a peptide which is known to undergo addition of a sugar chain is synthesized or amplified by PCR. The resultant oligonucleotide is incorporated at the 5' end of a plasmid coding for a heparin-binding protein.

As the secretion signal and the peptide which is known to undergo addition of a sugar chain, an amino terminal of a typical secretion-type glycoprotein may be used, for example. Specifically, the amino acid consisting of the N terminal 40 residues of mouse FGF-6 may be used.

The plasmid coding for a heparin-binding protein can be prepared by incorporating a DNA coding for the heparin-binding protein into an appropriate plasmid. As the plasmid into which a DNA coding for a heparin-binding protein is to be incorporated, any plasmid may be used as long as it is replicated and maintained in a host. For example, pBR322 and pUC18 from *E. coli* and pET-3c which was constructed based on these plasmids may be enumerated.

As a method for incorporating the above-described oligonucleotide into the plasmid coding for a heparin-binding protein, the method described in T. Maniatis et al., *Molecular Cloning*, Cold Spring Harbor Laboratory, p. 239 (1982) may be given, for example.

From the thus prepared plasmid, a region comprising a nucleotide sequence coding for a secretion signal, a peptide which is known to undergo addition of a sugar chain and a heparin-binding protein (hereinafter, referred to as a "region comprising a nucleotide sequence coding for a sugar chain-added heparin-binding protein") is cut out. This region is ligated to the downstream of a promoter in a vector suitable for expression to thereby obtain an expression vector.

The above-described region comprising a nucleotide sequence coding for a sugar chain-added heparin-binding protein may have ATG at its 5' end as a translation initiation codon and TAA, TGA or TAG at its 3' end as a translation termination codon. In order to express the protein encoded in the coding region, a promoter is ligated to the upstream of the region. As the promoter to be used in the present invention, any promoter may be used as long as it is appropriate to the host used for the expression of the gene. When the host to be transformed is a *bacillus*, SP01 promoter, SP02 promoter, penP promoter or the like may be used. When the host is a yeast, PH05 promoter, PGK promoter, GAP promoter, ADH promoter or the like may be used. When the host is an animal cell, a promoter from SV40 or a promoter from a retrovirus may be used.

As the plasmid into which the thus constructed recombinant DNA comprising a nucleotide sequence coding for a sugar chain-added heparin-binding protein is to be incorporated, any plasmid may be used as long as it can be expressed in the host cell. For example, those vectors which were constructed based on *E. coli*-derived pBR322 and pUC18 may be given.

As a method for incorporating the recombinant DNA into a plasmid, the method described in T. Maniatis et al., *Molecular Cloning*, Cold Spring Harbor Laboratory, p. 239 (1982) may be given, for example.

By introducing a vector comprising the above-described recombinant DNA into a host cell, a transformant carrying the vector is prepared.

As the host cell, any cell may be used as long as it has a sugar chain addition pathway. Specific examples include, but are not limited to, bacilli (e.g. *Bacillus subtilis*: DB105), yeasts (e.g. *Pichia pastoris: Saccharomyces cerevisiae*, animal cells (e.g. COS cell, CHO cell, BHK cell, NIH3T3 cell, BALB/c3T3 cell, HUVE cell, LEII cell) and insect cells (e.g. Sf-9 cell, Tn cell).

The above-mentioned transformation may be performed by a conventional method commonly used for each host. Alternatively, an applicable method may be used though it is not commonly used. For example, when the host is a yeast, a vector comprising the recombinant DNA is introduced into competent cells (prepared by the lithium method or the like) by the temperature shock method or electroporation. When the host is an animal cell, a vector comprising the recombinant DNA is introduced into cells at the logarithmic growth phase or the like by the calcium phosphate method, lipofection or electroporation.

By culturing the thus obtained transformant in a medium, a sugar chain-added heparin-binding protein is produced. As the medium for culturing the transformant, a conventional medium commonly used for each host may be used. Alternatively, an applicable medium may be used even if it is not commonly used. For example, when the host is a yeast, YPD medium or the like may be used. When the host is an animal cell, Dulbecco's MEM supplemented with animal serum, or the like may be used. The cultivation may be performed under conditions commonly employed for each host. Alternatively, applicable conditions may be used even if they are not commonly used. For example, when the host is a yeast, the cultivation is carried out at about 25-37° C. for about 12 hours to 2 weeks. If necessary, aeration or agitation may be carried out. When the host is an animal cell, the cultivation is carried out at about 32-37° C. under 5% $CO_2$ and 100% humidity for about 24 hours to 2 weeks. If necessary, the conditions of the gas phase may be changed or agitation may be carried out.

In order to obtain a sugar-chain added heparin-binding protein from the culture of the above-described transformant, the protein released into the culture fluid may be directly recovered from a supernatant after centrifugation. Alternatively, when the protein is to be extracted from the cultured microorganisms or cells, the protein may be obtained by disrupting the cultured microorganisms or cells with a homogenizer, a French press, ultrasonic waves, lysozyme and/or by freeze-thawing to thereby elute the protein of interest to the outside of the cells, and then recovering the protein from soluble fractions. If the protein of interest is contained in insoluble fractions, insoluble fractions may be recovered by centrifugation after disruption of the microorganisms or cells and then solubilized with a buffer containing guanidine hydrochloride or the like, to thereby recover the protein of interest from the resultant soluble fractions. Alternatively, the cultured microorganisms or cells may be disrupted by a direct treatment with a buffer containing a protein denaturing agent such as guanidine hydrochloride to thereby elute the protein of interest to the outside of the cells.

In order to purify a sugar chain-added heparin-binding protein from the above-mentioned supernatant, known separation/purification methods may be used in an appropriate combination. Specific examples of these known separation/purification methods include salting out, solvent precipitation, dialysis, ultrafiltration, gel filtration, SDS-polyacrylamide gel electrophoresis, ion exchange chromatography, affinity chromatography, reversed phase high performance liquid chromatography and isoelectric focusing. Further, affinity chromatography using heparin sepharose as a carrier may be applicable to a large number of heparin-binding proteins.

The thus obtained sample may be dialyzed and freeze-dried to obtain dry powder if the activity of the sugar chain-added heparin-binding protein is not damaged by such processing. Further, in storing the sample, addition of serum albumin to the sample is effective for preventing adsorption of the sample to the container.

The inclusion of an extremely small amount of a reducing agent in the purification process or the storing process is preferable for preventing oxidation of the sample. As the reducing agent, β-mercaptoethanol, dithiothreitol, glutathione or the like may be used.

The sugar chain-added heparin-binding protein of the invention may also be produced by attaching a sugar chain to a heparin-binding protein by a chemical method. As the specific method, the following a) or b), or a combination thereof may be used.

a) For example, first, a sugar chain is completed by a biological method, a chemical synthesis method or a combination thereof. At that time, a residue appropriate for protein binding may be introduced at one end of the sugar chain. For example, an aldehyde group is formed by reducing and partially oxidizing the reducing end of the completed sugar chain. Then, this aldehyde group is attached to an amino group in a protein by an amino bond to thereby complete the joining of the sugar chain and the protein.

b) For example, first, an aldehyde group is formed by reducing and partially oxidizing the reducing end of a monosaccharide or a residue appropriate for protein binding which is bound to a monosaccharide. Then, this aldehyde group is attached to an amino group in a protein by an amino bond to thereby complete the joining of the monosaccharide and the protein. An additional monosaccharide or sugar chain is attached to a hydroxyl group or the like of the above monosaccharide to thereby complete a sugar chain. For this attachment, a biological method, a chemical synthesis method or a combination thereof may be considered.

A heparin-binding protein functionalized by covalently bonding thereto a sugar chain can be used as a medicine. For example, the sugar chain-added heparin-binding protein of the invention regulates the physiological function of FGF. Specifically, the physiological function of FGF is to promote or inhibit the growth of fibroblast, vascular endothelial cell, myoblast, cartilage cell, osteoblast and glia cell. Therefore, the sugar chain-added heparin-binding protein of the invention is effective for promoting cell growth and tissue regeneration in liver or the like; for curing wounds and regulating nervous function; and for regulating the growth of fibroblast or the like. The protein of the invention is useful for preventing or treating various diseases such as fibroblastoma, angioma, osteoblastoma, death of neurocytes, Alzheimer's disease, Parkinson's disease, neuroblastoma, amnesia, dementia and myocardial infarction. The protein of the invention can also be used as a trichogenous agent or a hair-growing agent.

The sugar chain-added heparin-binding protein obtained as described above may be formulated into pharmaceutical compositions such as liquid, lotions, aerosols, injections, powder, granules, tablets, suppositories, enteric coated tablets and capsule, by mixing the protein with pharmaceutically acceptable solvents, vehicles, carriers, adjuvants, etc. according to conventional formulation methods.

The content of the sugar chain-added heparin-binding protein, which is an active ingredient, in the pharmaceutical composition may be about 0.0000000001 to 1.0% by weight.

The pharmaceutical composition can be administered parenterally or orally to mammals, e.g. human, mouse, rat, rabbit, dog, cat, etc. in a safe manner. The dose of the pharmaceutical composition may be appropriately changed depending on the dosage form, administration route, conditions of the patient and the like. For example, for administration to mammals including human, 0.0001 to 100 mg of the sugar chain-added heparin-binding protein may be applied to the diseased part several times a day.

The present invention has been described so far taking heparin-binding proteins as an example. However, it should be noted that besides the heparin-binding proteins, natural proteins having no sugar chain can also be functionalized by covalently bonding thereto a sugar chain.

Deposit of Microorganisms

Clones of *E. coli* DH5α carrying plasmids incorporating genes coding for the sugar chain-added heparin-binding proteins of the invention (having the DNA sequences of SEQ ID NOS: 2, 4, 18, 20, 22, 24, 26, 28 and 30, respectively) were deposited at the National Institute of Bioscience and Human-technology, Agency of Industrial Science and Technology under Accession Numbers of FERM BP-6428, FERM BP-6424, FERM BP-6427, FERM BP-6431, FERM BP-6429, FERM BP-6430, FERM BP-6423, FERM BP-1625 and FERM BP-6426 on Sep. 10, 1997.

Hereinbelow, the present invention will be described specifically with reference to the following Example. However, the present invention is not limited to this Examples.

EXAMPLE 1

1) Construction of S/FGF-1a-II Plasmid

1. Preparation of a Human Ryudocan cDNA Fragment phR7A8 is a plasmid obtained by inserting a human ryudocan cDNA (PCR product) into the EcoR V site of pBluescript II (KS+) cloning vector. This plasmid contains a partial sequence from position 7 to position 2610 in the mRNA sequence shown under Accession No. D13292 (see B.B.R.C. Vol. 190, No. 3, pp. 814-822, 1993).

This plasmid was digested with Pvu II. Using the resultant DNA fragment of 2,232 base pairs as a template, a PCR (polymerase chain reaction) was performed. As primers, #109 (5'-TTG TCG ACC CAC CAT GGC CCC CGC CCG TCT-3') (SEQ ID NO: 7) and #111 (5'-TTG ATA TCT AGA GGC ACC AAG GGA TG-3') (SEQ ID NO: 8) were used. The specifically amplified 276 bp band was separated by electrophoresis. After extraction, this fragment was double-digested with EcoR V and Sal I. The resultant 268 bp band was separated, extracted and then used in the ligation described below.

2. FGF-1a/pBluescript II (KS+)

A PCR was performed using human FGF-1 cDNA as a template and #967 (5'-GCG TCG ACA GCG CTA ATT ACA AGA AGC CCA AAC TC-3') (SEQ ID NO: 9) and #630 (5'-CCG AAT TCG AAT TCT TTA ATC AGA AGA GAC TGG-3') (SEQ ID NO: 10) as primers. The specifically amplified 434 bp band was separated by electrophoresis. After extraction, this fragment was double-digested with EcoR I and Sal I. The resultant 422 bp band was separated, extracted and then inserted into pBluescript II (KS+) cloning vector (2934 bp) double-digested with EcoR I and Sal I, where upon FGF-1a/pBluescript II (KS+) was produced.

FGF-1a/pBluescript II (KS+) was digested with Aor51H I and Sal I in this order. The resultant 2626 bp band was separated, extracted and then used in the ligation described below.

3. Preparation of S/FGF-1a-II Chimeric Gene

EcoR V/Sal I fragment (a PCR product from human ryudocan) and Aor51H I/Sal I fragment from FGF-1a/pBluescript II (KS+) were subjected to a DNA ligation to produce S/FGF-1a-II/pBluescript II (KS+) vector.

Subsequently, this vector was double-digested with EcoR I and Sal I to give a 678 bp band, which was then separated and extracted. The resultant fragment was inserted into pMEXneo expression vector (5916 bp) double-digested with EcoR I and Sal I, where upon S/FGF-1a-II/pMEXneo was produced. This expression vector comprises the nucleotide sequence shown in SEQ ID NO: 2.

2) Expression of S/FGF-1a-II

The resultant S/FGF-1a-II/pMEXneo was transferred into CHO-K1 cells (Chinese hamster ovary cell K1 substrain) by lipofection. Then, the cells were cultured in the presence of Geneticin to select gene-transferred cells. The selected cells were grown until the culture plate became almost full. Then, the medium was exchanged with a serum-free medium to increase the substance productivity of the cells. Thereafter, the medium was exchanged with a fresh one every two days. The resultant conditioned medium was subjected to low speed centrifugation, and the resultant supernatant was stored at 4° C.

3) Construction of N-FGF-6/1a-IV Plasmid

1. Preparation of a Mouse FGF-6 cDNA Fragment

A PCR was performed using mouse FGF-6 cDNA as a template and #1048 (5'-GCG TCG ACC CAC CAT GTC CCG GGG AGC AGG ACG TGT TCA GGG CAC GCT-GCA GGC TCT CGT CTT C-3') (SEQ ID NO: 11) and #968 (5'-GCG ATA TCC AGT AGC GTG CCG TTG GCG CG-3') (SEQ ID NO: 12) as primers. The specifically amplified 138 bp band was separated by electrophoresis. After extraction, this fragment was double-digested with EcoR V and Sal I. The resultant 130 bp band was separated, extracted and then used in the ligation described below.

2. Preparation of N-FGF-6/1a-IV Chimeric Gene

EcoR V/Sal I fragment (a PCR product from mouse FGF-6) and Aor51H I/Sal I fragment from FGF-1a/pBluescript II (KS+) were subjected to a DNA ligation to produce N-FGF-6/1a-IV/pBluescript II (KS+) vector. Subsequently, this vector was double-digested with EcoR I and Sal I to give a 540 bp band, which was then separated and extracted. The resultant fragment was inserted into pMEXneo expression vector (5916 bp) double-digested with EcoR I and Sal I, where upon N-FGF-6/1a-IV/pMEXneo was produced. This expression vector comprises the nucleotide sequence shown in SEQ ID NO: 4.

4) Expression of N-FGF-6/1a-IV

N-FGF-6/1a-IV was secreted into a culture supernatant by transferring N-FGF-6/1a-IV/pMEXneo into CHO-K1 cells in the same manner as described above for S/FGF-6/1a-II.

5) Construction of O-FGF-6/1a Plasmid

1. Preparation of N-FGF-6/1a<NQ> Chimeric Gene

A PCR was performed using N-FGF-6/1a/pBluescript II (KS+) vector as a template and #105 (5'-GCG TCG ACC CAC CAT GTC-3') (SEQ ID NO: 13) and #124 (5'-GCG ATA TCC AGT AGC GTG CCT TGG GCG CG-3') (SEQ ID NO: 14) as primers. The specifically amplified 138 bp band was separated by electrophoresis. After extraction, this fragment was double-digested with EcoR V and Sal I. The resultant 130 bp band was subjected to the ligation described below together with Aor51H I/Sal I fragment from FGF-1a/pBluescript II (KS+), to thereby yield N-FGF-6/1a<NQ>/pBluescript II (KS+) vector.

2. Preparation of O-FGF-6/1a Chimeric Gene

A primary PCR was performed using N-FGF-6/1a<NQ>/pBluescript II (KS+) vector as a template and #098 (5'-GCT GGA GGA GGC TGC TAC TCC AGC TCC AAA CCA TTA CA-3') (SEQ ID NO: 15) and #116 (5'-GCC GCT CTA GAA CTA GTG GAT-3') (SEQ ID NO: 16) as primers. The specifically amplified 210 bp band was purified. Using this PCR product and #115 (5'-AAC AAA AGC TGG GTA CCG GG-3') (SEQ ID NO:31) as primers, a secondary PCR was performed. The specifically amplified 631 bp band was separated by electrophoresis. After extraction and purification, this fragment was double-digested with EcoR I and Sal I. The resultant 558 bp band was separated, extracted and then inserted into pMEXneo expression vector (5916 bp) double-digested with EcoR I and Sal I, to thereby yield O-FGF-6/1a/pMEXneo. This expression vector comprises the nucleotide sequence shown in SEQ ID NO: 6.

6) Expression of O-FGF-6/1a

O-FGF-6/1a was secreted into a culture supernatant by transferring O-FGF-6/1a/pMEXneo into CHO-K1 cells in the same manner as described above for S/FGF-1a-II.

7) Expression of FGF-1a in *E. coli*

The fragment from human FGF-1a cDNA obtained by double digestion with Eco RI and Sal I as described above was incorporated into an *E. coli* expression vector pET3c. *E. coli* BL21(DE3)pLysS was transformed with the resultant vector. Subsequently, the transformant at the logarithmic growth phase was stimulated with IPTG (isopropylthio-β-galactoside) to induce the expression of the transferred gene. The cells were collected and sonicated for disruption to thereby release FGF-1a, which was then recovered in a centrifugation supernatant.

8) Removal of N-Linked Sugar Chains by Peptide N-Glycosidase F Treatment

N-FGF-6/1a-II concentrated with heparin-Sepharose beads was boiled and eluted in an electrophoresis buffer, as will be described later (see Test Example 1). To a part of the resultant solution, NP-40 (final concentration: 1%), Tris-HCl buffer (pH 7.5) and peptide N-glycosidase F (0.3 U) were added and the mixture was kept at 37° C. overnight. Then, the solution was heated at 100° C. for 3 min to terminate the enzyme reaction. This reaction solution was analyzed by SDS-denatured electrophoresis, as will be described later.

Various S/FGF-1a and N-FGF-6/1a genes can be prepared by appropriately altering the PCR primers (#111 and #968) used in "1. Preparation of a Human Ryudocan cDNA Fragment" and "1. Preparation of a Mouse FGF-6 cDNA Fragment" in the above Example and by replacing the restriction enzyme EcoR V with an appropriate enzyme which would generate a blunt end. Examples of such cDNA sequences are shown in SEQ ID NOS: 8, 20, 22, 24, 26 and 28.

Various O-FGF-6/1a genes can be prepared by replacing the template used in the PCR in "2. Preparation of O-FGF-6/1a Chimeric Gene" above with S/FGF-1a-II/pBluescript II (KS+), N-FGF-6/1a-IV/pBluescript II (KS+) or the like, or by appropriately altering the PCR primers (#098, #116 and #115), or by a combination of the both methods. An example of such a cDNA sequence is shown in SEQ ID NO: 30.

TEST EXAMPLE 1

SDS-Denatured Electrophoresis

Figure 4:
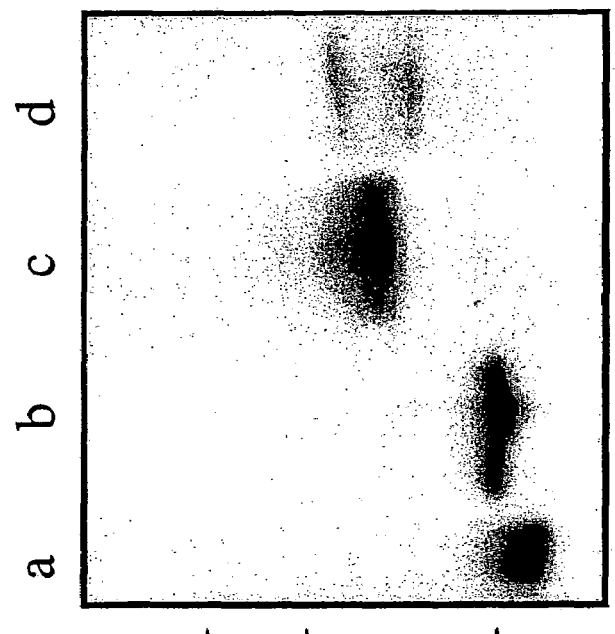
FIG. 4 shows SDS-denatured electrophoregrams of various S/FGF-1a-like proteins.
Figure 4:
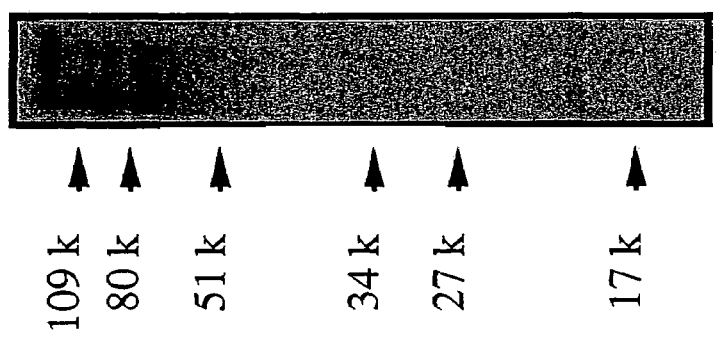

Heparin Sepharose beads added to conditioned media of various FGF-1a-like proteins-secreting cells were individually washed and then boiled directly with an electrophoresis buffer (containing SDS and 2-mercaptoethanol). The eluted protein was used as a sample. This sample was electrophoresed on 12.5% acrylamide gel in the presence of SDS and 2-mercaptoethanol. After being electrically transferred onto a nitrocellulose membrane, the protein was stained with anti-FGF-1 monoclonal antibody and horseradish peroxidase-labelled anti-mouse IgG antibody, followed by detection by the chemiluminescence method (FIG. 4). In the Figure, the arrows at the left side indicate the locations of standard proteins with known molecular weights and their molecular weights (in daltons). Panel A) shows an SDS-denatured electrophoregram of S/FGF-1a-II. Panel B) shows SDS-denatured electrophoregrams of FGF-1a produced in *E. coli* (lane a); N-FGF-1a-IV obtained by treating N-FGF-6/1a-IV with peptide N-glycosidase F for removal of N-linked sugar chains (lane b); N-FGF-6/1a-IV (lane c) and O-FGF-6/1a (lane d).

TEST EXAMPLE 2

DNA Synthesis Promoting Activity

The cell cycle of HUVEC (human umbilical cord-derived vascular endothelial cell) stops even in the presence of 15% serum if growth factors such as FGF are lacking. S/FGF-1a-II, N-FGF-6/1a-IV, O-FGF-6/1a, or FGF-1a produced in *E. coli* was added to HUVEC in such a state. Eighteen hours later, radio-labelled thymidine was allowed to be taken up for 6 hours. The amount of radioactivity taken up into DNA during this period was regarded as indicating the amount of the newly synthesized DNA.

Figure 5:
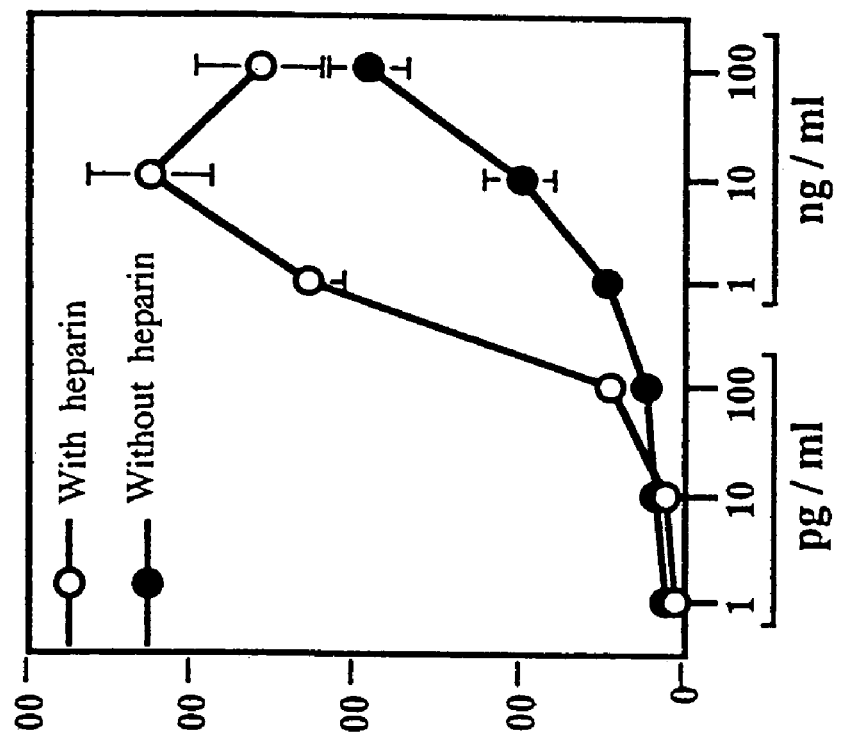
Figure 5:
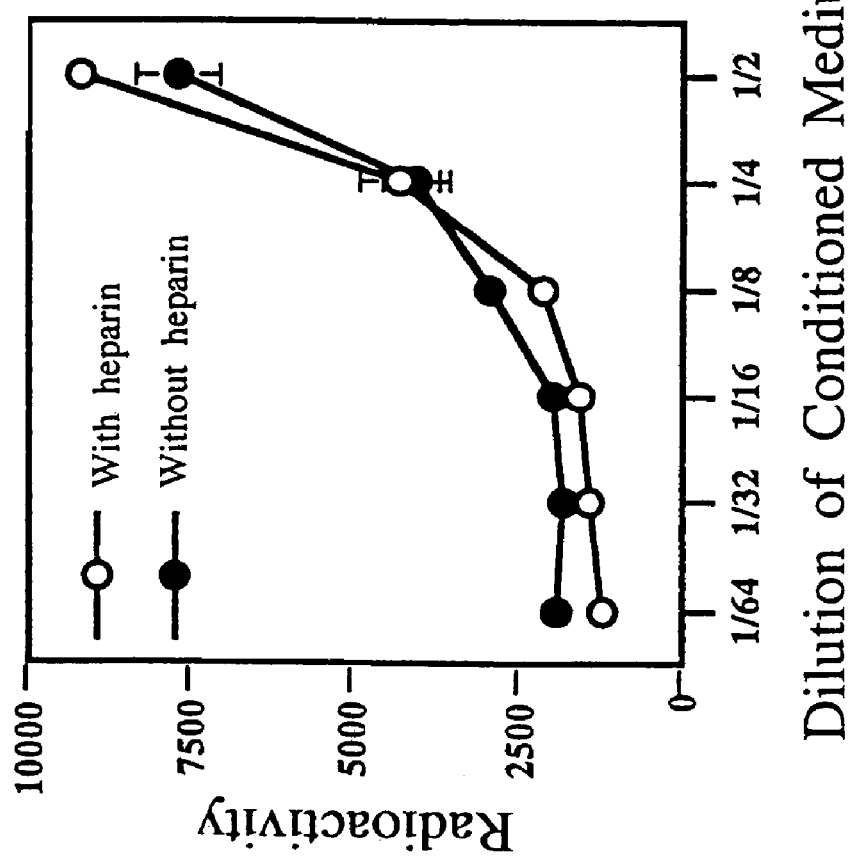

1. DNA Synthesis Promoting Effect (Heparin Non-Dependent) of S/FGF-1a-II on Human Vascular Endothelial Cell A conditioned medium was prepared from a serum-free medium of S/FGF-1a-II gene-transferred cells. This conditioned medium was dialyzed against PBS and then added to HUVEC in the presence (5 μg/ml) or absence of heparin, for examining the DNA synthesis promoting activity of S/FGF-1a-II on HUVEC. As a result, unlike FGF-1a produced in *E. coli*, S/FGF-1a-II promoted the DNA synthesis of HUVEC in a non-heparin-dependent manner (FIG. 5).

Figure 8:
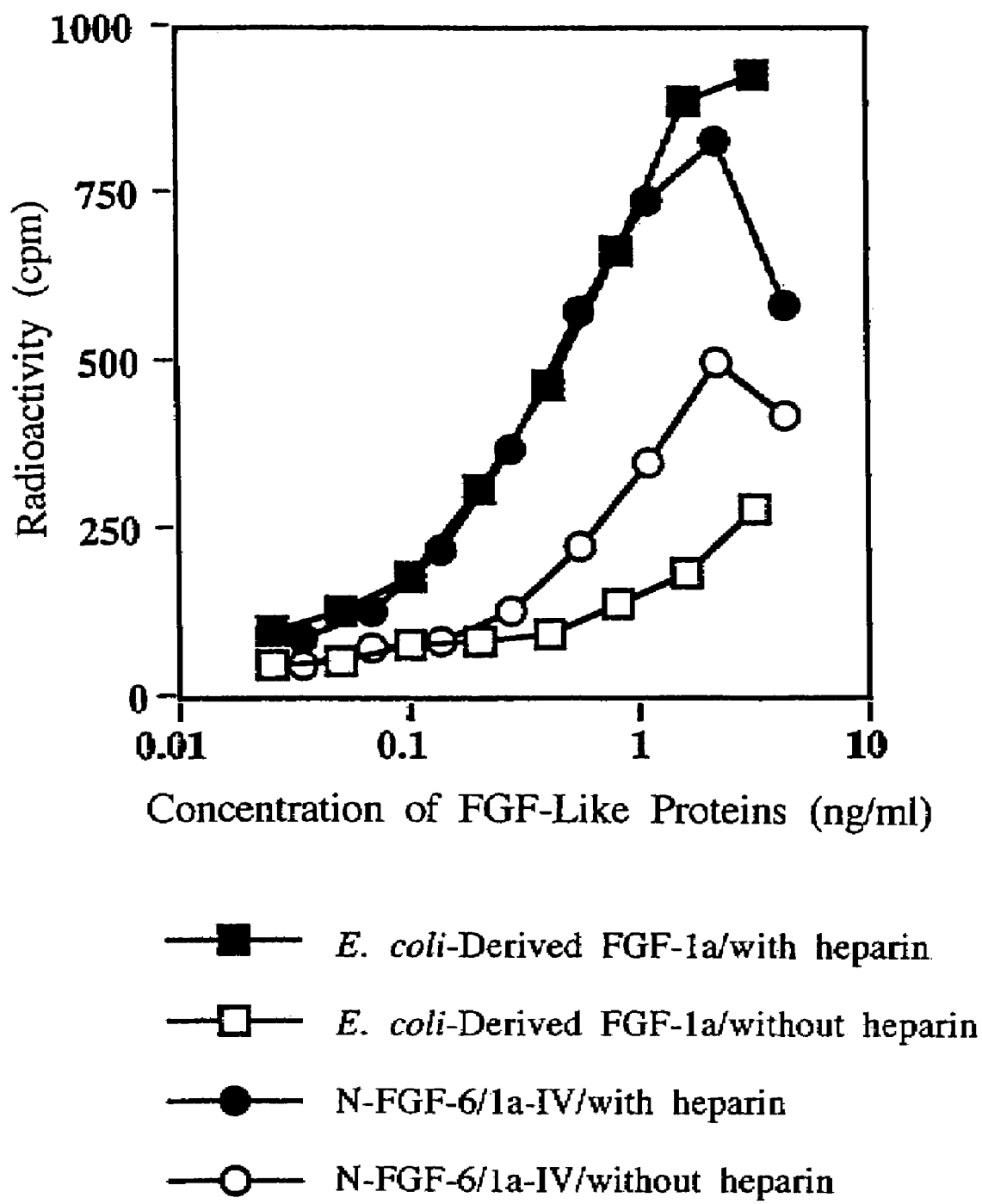

2. DNA Synthesis Promoting Effect of N-FGF-6/1a-IV on Human Vascular Endothelial Cell A conditioned medium was prepared from a serum-free medium of N-FGF-6/1a-IV gene-transferred cells. This conditioned medium was dialyzed against PBS and then added to HUVEC in the presence (5 μg/ml) or absence of heparin, for examining the DNA synthesis promoting activity of N-FGF-6/1a-IV on HUVEC. As a result, like FGF-1a produced in *E. coli*, N-FGF-6/1a-IV promoted the DNA synthesis of HUVEC. However, its heparin dependency was weak, and N-FGF-6/1a-IV exhibited stronger DNA synthesis promoting activity than FGF-1a from *E. coli* in the absence of heparin (FIG. 8).

TEST EXAMPLE 3

Heparin Affinity Chromatography

The heparin affinity of S/FGF-1a-II obtained in 2) in the above Example was examined. Heparin-Sepharose beads were added to a conditioned medium of S/FGF-1a-II-secreting cells and agitated at 4° C. for 2 hours or more. Beads precipitating by low speed centrifugation were recovered and washed sufficiently in physiological PBS (phosphate buffered saline, pH 7.4), followed by elution of the protein bound to heparin-fixed beads with PBS containing 2.5 M NaCl. After addition of distilled water to lower the salt concentration, this eluate was again applied to a high performance liquid chromatography column packed with heparin affinity beads. S/FGF-1a-II was eluted using NaCl density gradient.

Figure 9:
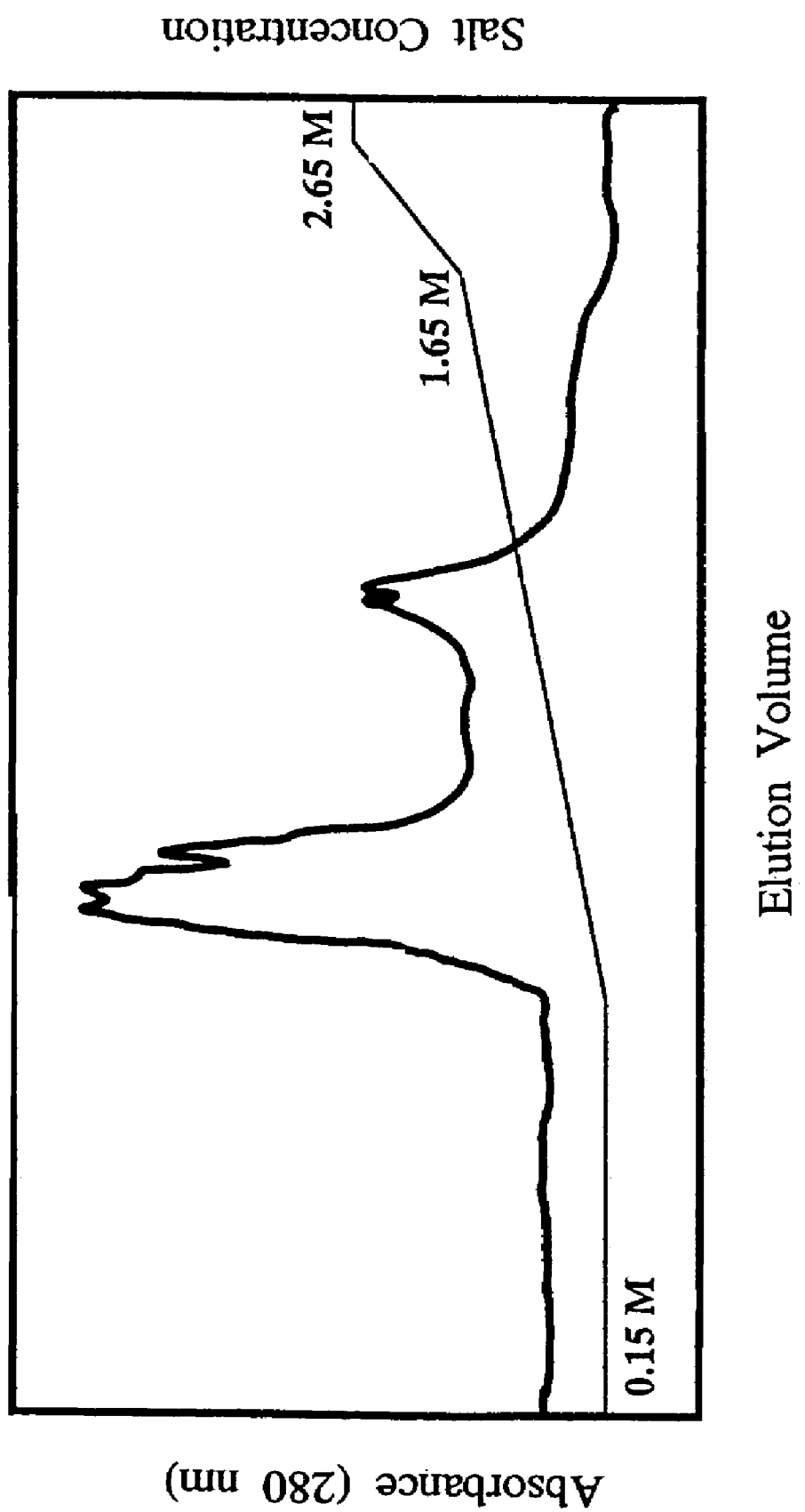
FIG. 9 shows the heparin affinity of S/FGF-1a-II.

While FGF-1a from E. coli was eluted at about 1.0 M NaCl, S/FGF-1a-II was eluted at about 0.4 M NaCl. Thus, it appears that affinity to the fixed heparin is lowered in S/FGF-1a-II (FIG. 9). The small peak seen around 1.0 M NaCl in FIG. 9 is considered to be a degradation product from S/FGF-1a-II as analyzed by SDS-denatured electrophoresis.

TEST EXAMPLE 4

Thermostability of FGF-1a-Like Proteins

Conditioned media of various FGF-1a-like protein-secreting cells were individually dialyzed against PBS sufficiently. A part of each of the resultant media was retained in PBS kept at 56° C. or 70° C. for 30 minutes, or retained at room temperature for 12 hours. Thereafter, the medium was re-dialyzed against PBS at 4° C. to prepare a sample. The stability of S/FGF-1a-II was determined by subjecting it to DNA synthesis promoting activity test on HUVEC after various treatments and then comparing the resultant activity with the activity of an S/FGF-1a-II sample dialyzed against PBS at 4° C. for 12 hours.

After retention at room temperature for 12 hours, even the activity of E. coli-derived FGF-1a was protected by heparin, but the activity of S/FGF-1a-II was protected regardless of the presence or absence of heparin.

Figure 6:
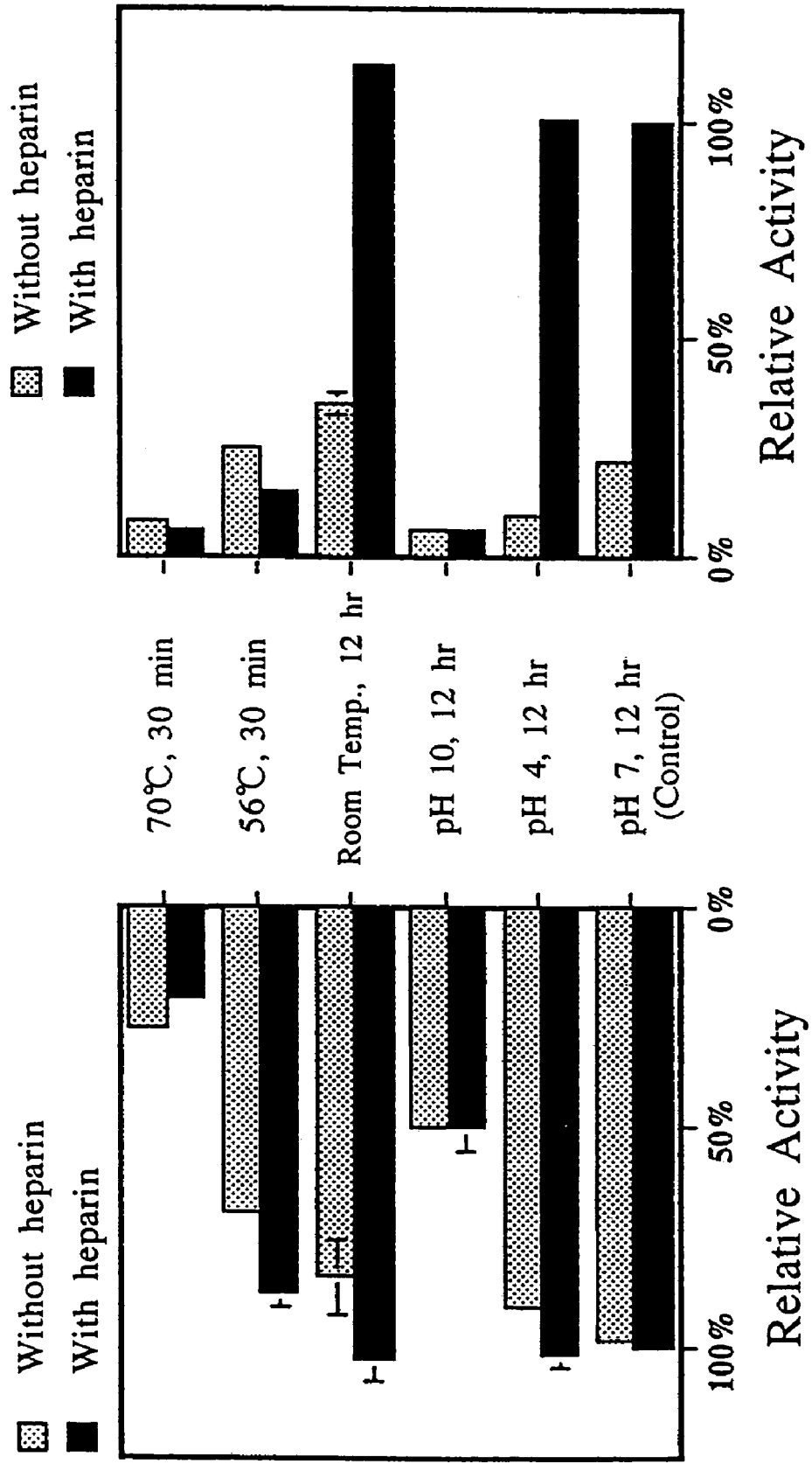

After heat treatment at 56° C. for 30 minutes, E. coli-derived FGF-1a was almost deactivated, but S/FGF-1a-II retained about 50% of the activity. Thus, it was considered that its thermostability was improved (FIG. 6).

TEST EXAMPLE 5

Acid Resistance and Alkali Resistance of FGF-1a-Like Proteins

Conditioned media of various FGF-1a-like protein-secreting cells were individually dialyzed against PBS sufficiently. A part of each of the resultant media was dialyzed in a citrate buffer (pH 4.0) or a sodium carbonate buffer (pH 10.0) for 12 hours and then re-dialyzed against PBS at 4° C. to prepare a sample. The stability of S/FGF-1a-II was determined by subjecting it to DNA synthesis promoting activity test on HUVEC after various treatments and then comparing the resultant activity with the activity of an S/FGF-1a-II sample dialyzed against PBS at 4° C. for 12 hours.

The activity of S/FGF-1a-II decreased little even after acid treatment at pH 4.0 regardless of the presence or absence of heparin; thus, an improvement in acid resistance was recognized (FIG. 6). After alkali treatment at pH 10.0, E. coli-derived FGF-1a was almost deactivated, but S/FGF-1a-II retained about 50% of the activity; thus, an improvement was also recognized in alkali resistance (FIG. 6).

TEST EXAMPLE 6

Stability of FGF-1a-Like Proteins Against Proteolytic Enzymes

Conditioned media of various FGF-1a-like protein-secreting cells were individually dialyzed against PBS sufficiently. To a part of each of the resultant media, trypsin solutions of varying concentrations (0.0001-0.1%) were added and kept at 37° C. for 1 hour. The thus obtained sample was subjected to the SDS-denatured electrophoresis described previously. The intensity of the remaining band was compared to the intensity of the band generated by the sample before trypsin treatment to give an indicator of stability.

Figure 7:
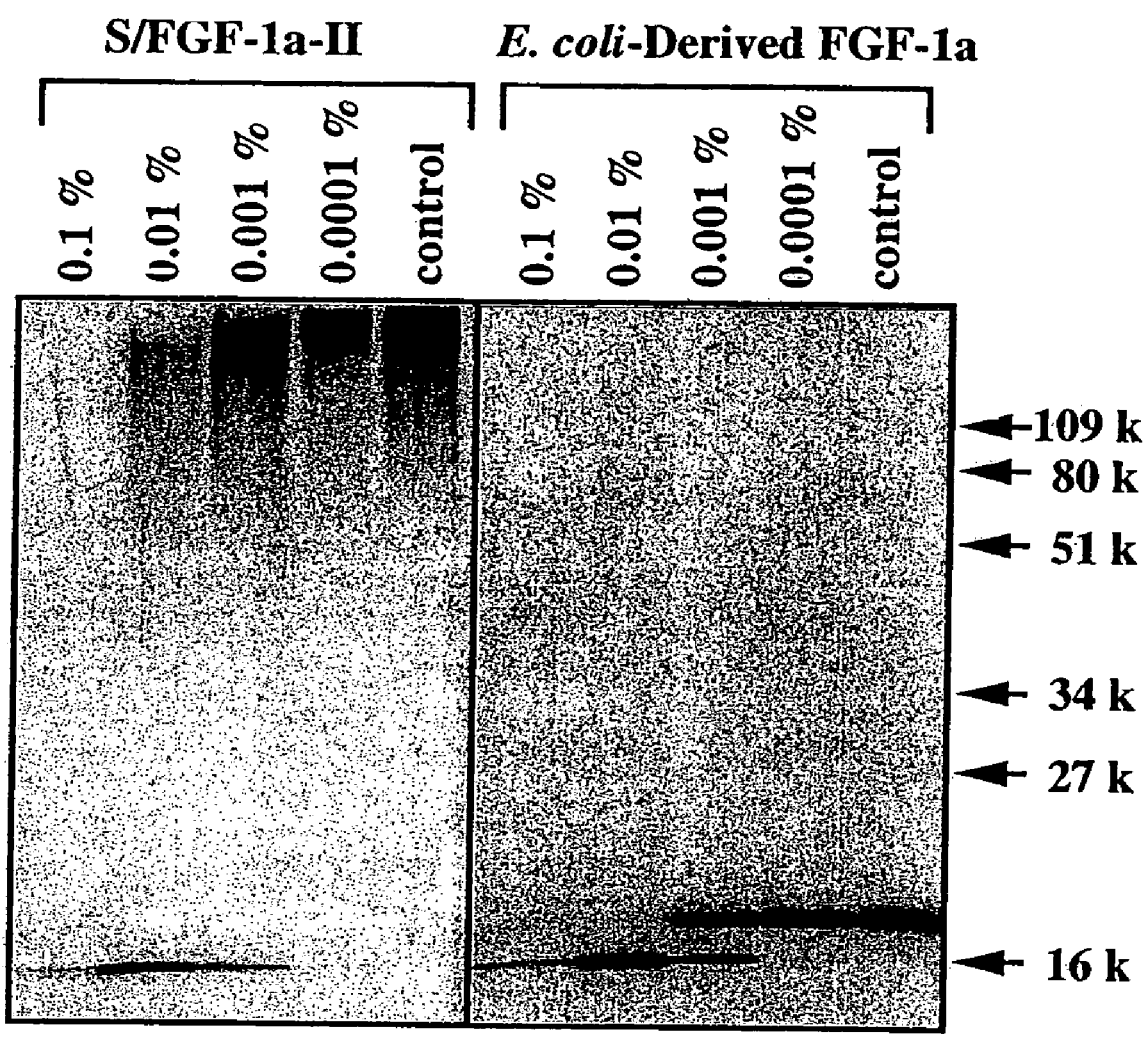

As a result, as shown in FIG. 7, 88% and 35% of the band intensity remained in S/FGF-1a-II after 0.001% and 0.01% trypsin treatment, respectively; however, the band intensity of E. coli-derived FGF-1a decreased to 58% and even to 6% after 0.001% and 0.01% trypsin treatment, respectively. Thus, it was considered that the resistance of S/FGF-1a-II to proteolytic enzymes was increased (FIG. 7).

The invention claimed is:

1. A functionalized heparin-binding protein comprising a heparin-binding protein and at least one sugar chain covalently bonded thereto,
wherein the at least one sugar chain is selected from the group consisting of a sulfated polysaccharide, a glycosaminoglycan, and an O-linked sugar chain,
wherein the DNA synthesis promoting activity of the heparin-binding protein is increased by adding the at least one covalently bonded sugar chain,
wherein the functionalized heparin-binding protein comprises the amino acid sequence of SEQ ID NO: 1, 17, 19, 21 or 23 and
wherein the at least one sugar chain is covalently bonded to the N-terminal peptide sequence of SEQ ID NO: 1, 17, 19, 21 or 23, wherein the N-terminal peptide sequence consists of residues 1-86 in SEQ ID NO: 1, residues 1-65 in SEQ ID NO: 17, residues 1-65 in SEQ ID NO: 19, residues 1-119 in SEQ ID NO: 21, and residues 1-146 in SEQ ID NO: 23.

2. The functionalized heparin-binding protein of claim 1, wherein the at least one sugar chain is heparan sulfate.

3. A pharmaceutical composition containing the functionalized heparin-binding protein of claim 1 as an active ingredient.

4. The functionalized heparin-binding protein of claim 1, wherein the at least one sugar chain is bonded to the heparin-binding protein at a site forming a turn in the secondary structure, or at a site at which addition of the sugar chain will not change the tertiary structure of said protein sufficiently to cause said protein to incur a loss of the DNA synthesis promoting activity.

5. A pharmaceutical composition containing the functionalized heparin-binding protein of claim 4 as an active ingredient.

6. A functionalized heparin-binding protein comprising a heparin-binding protein, comprising the amino acid sequence of SEQ ID NO: 1, 17, 19, 21 or 23, and a plurality of sugar chains covalently bonded thereto,
wherein the sugar chains are selected from the group consisting of a sulfated polysaccharide, a glycosaminoglycan, and an O-linked sugar chain,
wherein the sugar chains are covalently bonded to the N-terminal peptide sequence of said SEQ ID NO., thereby increasing the DNA synthesis promoting activity of the heparin-binding protein, and
wherein the N-terminal peptide sequence consists of residues 1-86 in SEQ ID NO: 1, residues 1-65 in SEQ ID NO: 17, residues 1-65 in SEQ ID NO: 19, residues 1-119 in SEQ ID NO: 21, and residues 1-146 in SEQ ID NO: 23.

7. The functionalized heparin-binding protein of claim 6, wherein at least one sugar chain out of the plurality of sugar chains is heparan sulfate.

8. A functionalized heparin-binding protein which comprises a heparin-binding protein modified with at least one covalently bonded sugar chain,
the sugar chain being selected from the group consisting of a sulfated polysaccharide, a glycosaminoglycan, and an O-linked sugar chain,
wherein the sugar chain is bonded at a Ser-Gly repeat sequence,
wherein the modified heparin-binding protein has improved stability over the unmodified protein, and
wherein the functionalized heparin-binding protein comprises the amino acid sequence of SEQ ID NO: 1, 17, 19, 21 or 23.

9. The functionalized heparin-binding protein of claim 8, wherein the sugar chain is heparan sulfate.

10. The functionalized heparin-binding protein of claim 8, wherein the stability is chosen from among the group consisting of thermostability, acid resistance, alkali resistance and resistance to proteolytic enzymes.

* * * * *